(12) United States Patent
Ji et al.

(10) Patent No.: US 11,666,555 B2
(45) Date of Patent: Jun. 6, 2023

(54) RELA INHIBITORS FOR BIOFILM DISRUPTION

(71) Applicants: Hai-Feng Ji, Cherry Hill, NJ (US); Garth David Ehrlich, Philadelphia, PA (US); Donald Carl Hall, Jr., Delta, PA (US); Jaroslaw E. Krol, Philadelphia, PA (US); John P. Cahill, Philadelphia, PA (US)

(72) Inventors: Hai-Feng Ji, Cherry Hill, NJ (US); Garth David Ehrlich, Philadelphia, PA (US); Donald Carl Hall, Jr., Delta, PA (US); Jaroslaw E. Krol, Philadelphia, PA (US); John P. Cahill, Philadelphia, PA (US)

(73) Assignee: DREXEL UNIVERSITY, Philadelphia, PA (US)

( * ) Notice: Subject to any disclaimer, the term of this patent is extended or adjusted under 35 U.S.C. 154(b) by 20 days.

(21) Appl. No.: 16/610,376

(22) PCT Filed: May 14, 2018

(86) PCT No.: PCT/US2018/032560
§ 371 (c)(1),
(2) Date: Nov. 1, 2019

(87) PCT Pub. No.: WO2018/213185
PCT Pub. Date: Nov. 22, 2018

(65) Prior Publication Data
US 2020/0069647 A1  Mar. 5, 2020

Related U.S. Application Data

(60) Provisional application No. 62/507,526, filed on May 17, 2017.

(51) Int. Cl.
*A61K 31/415* (2006.01)
*A61K 45/06* (2006.01)
(Continued)

(52) U.S. Cl.
CPC .......... *A61K 31/415* (2013.01); *A61K 31/341* (2013.01); *A61K 31/43* (2013.01);
(Continued)

(58) Field of Classification Search
CPC .... A61K 31/415; A61K 31/341; A61K 45/06; A61K 31/496; A61K 31/506
See application file for complete search history.

(56) References Cited

U.S. PATENT DOCUMENTS 6,608,087 B1   8/2003   Charifson et al.
6,632,809 B2   10/2003  Grillot et al.
(Continued)

OTHER PUBLICATIONS

Wexselblatt, E. et al., PLoS Pathogens, 2012, vol. 8, No. 9, e1002925, internal pp. 1-10. (Year: 2012).*
(Continued)

*Primary Examiner* — Craig D Ricci
*Assistant Examiner* — Janet L Coppins
(74) *Attorney, Agent, or Firm* — Mendelsohn Dunleavy, P.C.

(57) ABSTRACT

Pharmaceutical compositions comprising a RelA enzyme inhibitor and a bactericidal antibiotic, wherein said RelA enzyme inhibitor binds to the RelA enzyme in bacteria to reduce biofilm formation and to degrade biofilms that have been formed. The pharmaceutical compositions can be used to treat bacterial biofilm diseases.

6 Claims, 9 Drawing Sheets

(51) Int. Cl.
- A61K 31/341 (2006.01)
- A61K 31/43 (2006.01)
- A61K 31/496 (2006.01)
- A61K 31/506 (2006.01)
- A61K 31/7008 (2006.01)
- C07D 231/12 (2006.01)
- C07D 307/20 (2006.01)

(52) U.S. Cl.
CPC .......... *A61K 31/496* (2013.01); *A61K 31/506* (2013.01); *A61K 31/7008* (2013.01); *C07D 231/12* (2013.01); *C07D 307/20* (2013.01)

(56) References Cited

U.S. PATENT DOCUMENTS

| | | | |
|---|---|---|---|
| 8,343,966 B2 * | 1/2013 | Adcock | A61P 31/14 544/131 |
| 2004/0043989 A1 | 3/2004 | Grillot et al. | |
| 2005/0054697 A1 | 3/2005 | Yager et al. | |
| 2009/0264342 A1 | 10/2009 | Cottarel et al. | |
| 2011/0172174 A1 | 7/2011 | Andersen et al. | |

OTHER PUBLICATIONS

Anderson, Chemistry & Biology, vol. 10, (2003), 787-797. (Year: 2003).*

Look, Gary C., et al. "The discovery of biaryl acids and amides exhibiting antibacterial activity against Gram-positive bacteria." Bioorganic & Medicinal Chemistry Letters 14.6 (2004): 1423-1426 (Year: 2004).*

Thiel, Nature Biotechnology vol. 22 (5), (2004), 513-519. (Year: 2004).*

Wexselblatt, Ezequiel, et al. "Design, synthesis and structure-activity relationship of novel Relacin analogs as inhibitors of Rel proteins." European Journal of Medicinal Chemistry 70 (2013): 497-504 (Year: 2013).*

Tuttle, Marie S., et al. "Characterization of Bacterial Communities in Venous Insufficiency Wounds by Use of Conventional Culture and Molecular Diagnostic Methods." Journal of Clinical Microbiology 49.11 (2011): 3812-3819.

Wexselblatt, Ezequiel, et al. "Design, synthesis and structure—activity relationship of novel Relacin analogs as inhibitors of Rel proteins." European Journal of Medicinal Chemistry 70 (2013): 497-504.

Wexselblatt, Ezequiel, et al. "Relacin, a Novel Antibacterial Agent Targeting the Stringent Response." PLoS Pathogens 8.9 (2012): e1002925. (10 pages).

Wolcott, Randall D., and Garth D. Ehrlich. "Biofilms and chronic infections." Jama 299.22 (2008): 2682-2684.

International Search Report and Written Opinion for International Application No. PCT/US2018/032560; dated Sep. 4, 2018 (13 pages).

Albesa, Inés, et al. "Oxidative stress involved in the antibacterial action of different antibiotics." Biochemical and Biophysical Research Communications 317.2 (2004): 605-609.

Yarwood, Jeremy M., et al. "Quorum sensing in *Staphylococcus* infections." The Journal of Clinical Investigation 112.11 (2003): 1620-1625.

Godfrey, Henry P. et al., "The role of the stringent response in the pathogenesis of bacterial infections." Trends in Microbiology 10.8 (2002): 349-351.

Høiby, Niels, et al. "Antibiotic resistance of bacterial biofilms." International Journal of Antimicrobial Agents 35.4 (2010): 322-332.

Kudrin, Pavel, et al. "Subinhibitory concentrations of bacteriostatic antibiotics induce relA-dependent and relA-independent tolerance to β-lactams." Antimicrobial Agents and Chemotherapy 61.4 (2017): e02173-16.

Boissy, Robert, et al. "Comparative supragenomic analyses among the pathogens *Staphylococcus aureus*, *Streptococcus pneumoniae*, and *Haemophilus influenzae* using a modification of the finite supragenome model." BMC genomics 12.1 (2011): 187-202.

Brown, Alan, et al. "Ribosome-dependent activation of stringent control." Nature 534.7606 (2016): 277-280.

Bunders, Cynthia A., et al. "Identification of aryl 2-aminoimidazoles as biofilm inhibitors in Gram-negative bacteria." Bioorganic & Medicinal Chemistry Letters 20.12 (2010): 3797-3800.

Capoor, Manu N., et al. "Prevalence of Propionibacterium acnes in intervertebral discs of patients undergoing lumbar microdiscectomy: a prospective cross-sectional study." PloS ONE 11.8 (2016): e0161676.

Cegelski, Lynette, et al. "Small-molecule inhibitors target *Escherichia coli* amyloid biogenesis and biofilm formation." Nature Chemical Biology 5.12 (2009): 913-919.

Cheng, Kenneth, et al. "Inhibitory Concentrations of Kanamycin in the presence of ppGpp synthase RelA Confer Protection Against Subsequent lethal Antibiotic Assaults in *E. coli* CP78." Journal of Experimental Microbiology and Immunology 14 (2010): 51-56.

Davies, David. "Understanding biofilm resistance to antibacterial agents." Nature Reviews Drug Discovery 2.2 (2003): 114-122.

Davies, David G., et al. "The involvement of cell-to-cell signals in the development of a bacterial biofilm." Science 280.5361 (1998): 295-298.

Hall, Donald C. Jr., "Discovery, Design, and Synthesis of Small molecule RelA Inhibitors", Thesis Proposal, Drexel University, May 2017 (14 pages).

Ehrlich, Garth D. "Correlation of Molecular and Clinical Parameters of Human T-Lymphotropic Retroviral Infections", Dissertation Abstract, Syracuse University, Aug. 1987 (318 pages).

Ehrlich, Garth D., et al. "The distributed genome hypothesis as a rubric for understanding evolution in situ during chronic bacterial biofilm infectious processes." FEMS Immunology & Medical Microbiology 59.3 (2010): 269-279.

Ehrlich, Garth D., et al. "Bacterial plurality as a general mechanism driving persistence in chronic infections." Clinical Orthopaedics and Related Research 437 (2005): 20-24.

Ehrlich, Garth D., et al. "Mucosal biofilm formation on middle-ear mucosa in the chinchilla model of otitis media." JAMA 287.13(2002): 1710-1715.

Festing, M. F. W. et al., "Strain differences in haematological response to chloroamphenicol succinate in mice: implications for toxicological research." Food and Chemical Toxicology 39.4 (2001): 375-383.

Festing, Michael FW. "Inbred strains should replace outbred stocks in toxicology, safety testing, and drug development." Toxicologic Pathology 38.5 (2010): 681-690.

Fitzgerald, George et al. "Modified penicillin enrichment procedure for the selection of bacterial mutants." Journal of Bacteriology 122.1 (1975): 345-346.

Hall-Stoodley, Luanne, et al. "Direct detection of bacterial biofilms on the middle-ear mucosa of children with chronic otitis media." JAMA 296.2 (2006): 202-211.

Harro, Janette M., et al. "Vaccine development in *Staphylococcus aureus*: taking the biofilm phenotype into consideration." FEMS Immunology & Medical Microbiology 59.3 (2010): 306-323.

Hiller, N. Luisa, et al. "Comparative genomic analyses of seventeen *Streptococcus pneumoniae* strains: insights into the pneumococcal supragenome." Journal of Bacteriology 189.22 (2007): 8186-8195.

Hiller, N. Luisa, et al. "Generation of genic diversity among *Streptococcus pneumoniae* strains via horizontal gene transfer during a chronic polyclonal pediatric infection." PLoS Pathogens 6.9 (2010): e1001108 (14 pages).

Hogg, Justin S., et al. "Characterization and modeling of the Haemophilus influenzae core and supragenomes based an the complete genomic sequences of Rd and 12 clinical nontypeable strains." Genome Biology 8.6 (2007): R103. (18 pages).

Jacovides, Christina L., et al. "Successful identification of pathogens by polymerase chain reaction (PCR)-based electron spray ionization time-of-flight mass spectrometry (ESI-TOF-MS) in culture-negative periprosthetic joint infection." Journal of Bone and Joint Surgery, 94.24 (2012): 2247-2254.

Kohanski, Michael A., et al. "A common mechanism of cellular death induced by bactericidal antibiotics." Cell 130.5 (2007): 797-810.

(56) References Cited

OTHER PUBLICATIONS

Kotb, Ahmed, et al. "Phenylthiazoles with tert-Butyl side chain: Metabolically stable with anti-biofilm activity." European Journal of Medicinal Chemistry 151 (2018): 110-120.

Kwok, Shirley et al. "Identification of Human Immunodeficiency Virus Sequences by Using In Vitro Enzymatic Amplification and Oligomer Cleavage Detection." Journal of Virology 61.5 (1987): 1690-1694.

Look, Gary C., et al. "The discovery of biaryl acids and amides exhibiting antibacterial activity against Gram-positive bacteria." Bioorganic & Medicinal Chemistry Letters 14.6 (2004): 1423-1426.

Nickel, J. Curtis, et al. "Search for Microorganisms in Men with Urologic Chronic Pelvic Pain Syndrome: A Culture-Independent Analysis in the MAPP Research Network." The Journal of Urology 194.1 (2015): 127-135.

Nickel, J. Curtis, et al. "Assessment of the Lower Urinary Tract Microbiota During Symptom Flare in Women with Urologic Chronic Pelvic Pain Syndrome: a MAPP Network Study." The Journal of Urology 195.2 (2016): 356-362.

Palmer, Michael P., et al. "Can We Trust Intraoperative Culture Results in Nonunions?." Journal of Orthopaedic Trauma 28.7 (2014): 384-390.

Pettit, Robin K., et al. "Microplate Alamar Blue Assay for *Staphylococcus epidemnidis* Biofilm Susceptibility Testing." Antimicrobial Agents and Chemotherapy 49.7 (2005): 2612-2617.

Post, J. Christopher, et al. "Molecular Analysis of Bacterial Pathogens in Otitis Media With Effusion." JAMA 273.20 (1995): 1598-1604.

Post, J. Christopher, et al. "PCR-Based Detection of Bacterial DNA After Antimicrobial Treatment is Indicative of Persistent, Viable Bacteria in the Chinchilla Model of Otitis Media." American Journal of Otolaryngology 17.2 (1996): 106-111.

Prabhakara, Ranjani, et al. "Murine Immune Response to a Chronic *Staphylococcus aureus* Biofilm Infection." Infection and Immunity 79.4 (2011): 1789-1796.

Rau, Martin H., et al. "Deletion and acquisition of genomic content during early stage adaptation of Pseudomonas aeruginosa to a human host environment." Environmental Microbiology 14.8 (2012): 2200-2211.

Rayner, Mark G., et al. "Evidence of Bacterial Metabolic Activity in Culture-Negative Otitis Media With Effusion." JAMA 279 (1998): 296-299.

Sapi, Eva, et al. "Characterization of Biofilm Formation by Borrelia burgdorferi in vitro." PloS one 7.10 (2012): e48277.

Sauer, Karin et al. "Biofilms and biocomplexity." Microbe-American Society for Microbiology 2.7 (2007): 347.

Sauer, Karin, et al. "Pseudomonas aeruginosa Displays Multiple Phenotypes during Development as a Biofilm." Journal of Bacteriology 184.4 (2002): 1140-1154.

Schooling, Sarah R., and Terry J. Beveridge. "Membrane Vesicles: an Overlooked Component of the Matrices of Biofilms." Journal of Bacteriology 188.16 (2006): 5945-5957.

Shaikh, Shafiq, et al. "Influence of tick and mammalian physiological temperatures on Borrelia burgdorferi biofilms." Microbiology 162.11 (2016): 1984-1995.

Shen K, et al, "Evidence-based Otitis Media" Rosenfeld R,& Bluestone CD (eds), Hamilton: B.C. Decker Inc. 91-119, 2003.

Stojicic, Sonja, et al. "Effect of the Source of Biofilm Bacteria, Level of Biofilm Maturation, and Type of Disinfecting Agent on the Susceptibility of Biofilm Bacteria to Antibacterial Agents" Journal of Endodontics 39.4 (2013): 473-477.

Stoodley, Paul, et al. "Structural Deformation of Bacterial Biofilms Caused by Short-Term Fluctuations in Fluid Shear: An In Situ Investigation of Biofilm Rheology." Biotechnology and Bioengineering 65.1 (1999): 83-92.

Theophilus, P. A. S., et al. "Effectiveness of Stevia Rebaudiana Whole Leaf Extract Against the Various Morphological Forms of Borrelia Burgdorferi in Vitro." European Journal of Microbiology & Immunology 5.4 (2015): 268-280.

* cited by examiner

RELA INHIBITORS FOR BIOFILM DISRUPTION

The present application claims priority to U.S. Provisional Application Ser. No. 62/507,526 filed May 17, 2017. U.S. Provisional Application Ser. No. 62/507,526 is incorporated herein by reference in its entirety.

FIELD OF THE DISCLOSURE

This disclosure relates to pharmaceutical compositions comprising a RelA enzyme inhibitor and a bactericidal antibiotic wherein said RelA enzyme inhibitor binds to the RelA enzyme in bacteria to reduce biofilm formation and to degrade biofilms that have been formed. The pharmaceutical compositions can be used to treat bacterial biofilm diseases.

BACKGROUND OF THE DISCLOSURE

The U.S. National Institutes of Health announced in the early 2000's that biofilms are detrimentally relevant in over 80% of infections in humans (Bryers, J. D., Medical Biofilms. *Biotechnology and bioengineering* 2008, 100 (1), 1-18). A biofilm is a collection of cells which have aggregated together in ordered structures, forming an extracellular polymeric matrix. These aggregates act as a single organism (Costerton et al., *The Journal of Clinical Investigation* 112 (10), 1466-1477). Individual bacterial cells, unless they are genetically resistant, are easily killed by current antibiotics. However, these same bacteria when growing as biofilms can be resistant to 1000 times the antibiotic concentrations. (Hall-Stoodley et al., *BMC Microbiology* 2008, 8 (1), 173). It has been demonstrated that the resistance of bacterial biofilms to antibiotics is metabolic, in that most bacteria in a biofilm are relatively metabolically inactive (Borriello et al., *Antimicrobial Agents and Chemotherapy* 2004, 48 (7), 2659-2664) and that this metabolic resistance can be partially overcome by providing fermentable substrates (Borriello et al., *Antimicrobial Agents and Chemotherapy* 2006, 50 (1), 382-384). Subsequently, Nguyen et al. (Nguyen et al., *Science* 2011, 334 (6058), 982) demonstrated that the metabolic resistance of biofilms to antibiotics was active, not passive, and relied on the bacterial stringent response by the protein RelA (a highly-conserved enzyme among gram-negative bacteria).

The stringent response can be defined as a systematic reaction to stresses placed on a cell or group of cells (Godfrey et al., *Trends in Microbiology* 2002, 10 (8), 349-351). The stresses that are often associated with the stringent response include starvation of essential amino acids, heat shock, iron limitation, population density, and oxidative stress (associated with antibiotic treatment), Godfrey 2002; Brown et al., *Nature* 2016, 534 (7606), 277-280; Albesa et al., *Biochemical and Biophysical Research Communications* 2004, 317 (2), 605-609); and Kudrin et al. *Antimicrobial Agents and Chemotherapy* 2017, 61 (4)). The bacterial cells' response to exposure to antibiotics is pleiotropic and leads to antibiotic resistance and the formation of bacteria biofilms.

The stringent response enzymatic pathway allows for the formation of ppGpp (guanosine tetraphosphate) and pppGpp (guanosine pentaphosphate) from GTP (guanosine triphosphate) (Chatterji et al., *Current Opinion in Microbiology* 2001, 4 (2), 160-165).

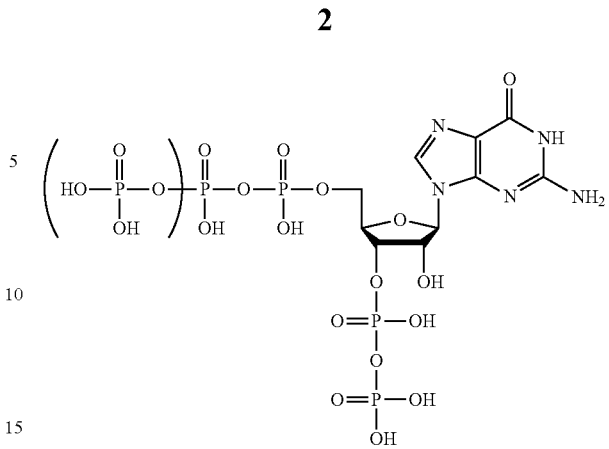

Guanosine (Penta)tetraphosphate

These ppGpp and pppGpp compounds have been labeled "alarmones" (or "magic spots") due to the understanding that these compounds alarm the cell to the detrimental conditions occurring. The increased levels of these two alarmones changes the cellular metabolism (Chatterji et al., 2001). This change in cellular metabolism and formation of biofilms allows a cell to go into a protective state. The combination of lowered metabolic rate and upregulation of protective enzymes in biofilms collectively make biofilm infections antibiotic resistant.

The resultant shift in metabolism turns the bacteria into the prokaryotic equivalent of a metazoan stem cell, termed a persister. The biofilm persister cells become resistant to antibiotics as they have already upregulated the enzymatic machinery to protect from the effects of antibiotics.

Stem cells and persisters owe their extraordinarily long-term survival to the upregulation of proteins associated with combating oxidative stress. This upregulation of protective factors is what gives biofilms their antibiotic-resistance phenotype (Nguyen 2011).

In the biofilm life cycle, the cells continue to multiply inside the biofilm until they reach a critical point and dispersion or planktonic showers (a release of planktonic cells into the host's system) occurs. If dispersion occurs, a host can be flooded with bacteria that can either form more biofilm colonies or lead to a systemic infection (Lebeaux et al., *Microbiology and Molecular Biology Reviews*, 2014, 78 (3), 510-543). Biofilms are one of the major causes of chronic infections because of their ability to re-infect a host.

Current methods for treatment of biofilm infections are mostly crude and mechanical in nature. These methods do not target the bacteria directly (Lebeaux 2014). The front-line technique in a clinical setting is hygiene of both the patients as well as the medical professionals. Biofilms tend to form on hard surfaces, which makes medical devices of great concern in biofilm infections (Potera et al., *Science* 1999, 283 (5409), 1837). The high rate of infections in hospitals often leads to infections that form biofilms, these infections are usually chronic in nature, which makes them difficult to treat.

Other treatments include removal of unnecessary devices such as unnecessary urinary catheters. Most of these devices contain an antibiotic coating to keep bacteria from colonizing and forming a biofilm before they are utilized in a medical application (Lebeaux 2014). These methods are not highly effective and only work if they are followed by every medical professional.

SUMMARY OF THE INVENTION

There is great need for antibacterial agents which fight against pathogenic bacteria. The most problematic of bacterial infections use the formation of biofilms as a survival strategy to adapt to hostile environments. Without being bound to theory, the present invention takes advantage of the property of certain compounds to inhibit the function of RelA and prevent the triggering of the stringent response. The stringent response in bacteria, associated with their developing stem cell/persister phenotypes, is triggered by the accumulation of the bacterial signaling molecules collectively called (p)ppGpp. Synthesis of (p)ppGpp has been characterized as a ribosome-dependent pyrophosphate transfer of the β and γ phosphates from an ATP donor to the 3' hydroxyl group of GTP or GDP (FIG. 1). In Gram-negative bacteria, (p)ppGpp is mostly synthesized by RelA and hydrolyzed by SpoT (Hauryliuk et al., *Nat Rev Micro* 13, 298-309, 2015; Potrykus et al., *Annual Review of Microbiology* 62, 35-51, 2008). The RelA protein catalyzes the reaction ATP+GTP→AMP+pppGpp; and the pppGpp is then rapidly converted to ppGpp by the gpp gene product. Inhibition of RelA impairs biofilm formation and increases sensitivity to antibiotics.

The inventive RelA inhibitors can act to prevent this reaction by inhibiting GTP from binding to an open form of RelA in the enzymatic pathway. The enzymatic pathway is discussed in Arenz et al. (*Nucleic acids research* 2016, 44 (13), 6471-81).

The rationale for this approach is that bacteria in which the RelA gene has been knocked out still form biofilms, but they will no longer be resistant to antibiotics. Thus, the RelA inhibitors can act to repotentiate antibiotics against biofilm bacteria. The RelA inhibitors of the present invention can affect biofilm formation and bacterial survival in biofilms when used with traditional antibiotics that are otherwise ineffective. Thus, the present invention can provide broad-range anti-biofilm treatments modalities which would be composed of the RelA inhibitors combined with (classical) bactericidal antibiotics.

In an aspect, the present invention provides a pharmaceutical composition comprising a RelA enzyme inhibitor and a bactericidal antibiotic, wherein said RelA enzyme inhibitor binds to RelA enzyme.

In each of the foregoing embodiments, the RelA enzyme inhibitor can bind to the RelA enzyme with a predicted binding score which is less than or equal to −9 kcal/mole; or a predicted binding score which is less than −9.5 kcal/mole; or a predicted binding score which is −13.57 to −9.5 kcal/mole.

In each of the foregoing embodiments, the RelA enzyme inhibitor can be selected from the group consisting of S3-G1A and S3-G1B as two examples, but the inhibitors are not limited to these two systems:

| Compound Structure | IUPAC Name | Assay Name |
|---|---|---|
| [structure of (4-chlorophenyl)([(3-(4-hydroxyphenyl)-1H-pyrazol-5-yl]carbonyl)amino)acetic acid] | (4-chlorophenyl)([(3-(4-hydroxyphenyl)-1H-pyrazol-5-yl]carbonyl)amino)acetic acid | S3-G1A |
| [structure of 3-(6-amino-5-cyano-4-[2-(propylamino)pyrimidin-5-yl]pyridin-2-yl))-1H-pyrazole-5-carboxylic acid] | 3-(6-amino-5-cyano-4-[2-(propylamino)pyrimidin-5-yl]pyridin-2-yl))-1H-pyrazole-5-carboxylic acid | S3-G1B | or a bioisostere of S3-G1A and S3-G1B; an enantiomer of S3-G1A, S3-G1B and the foregoing bioisosteres; a racemic mixture of enantiomers of S3-G1A and S3-G1B and the foregoing bioisosteres, or a pharmaceutically acceptable salt of S3-G1A and S3-G1B, the foregoing enantiomers, bioisosteres and racemic mixtures.

In each of the foregoing embodiments, the RelA enzyme inhibitor can be selected from the group consisting of a bioisostere of S3-G1A or S3-G1B an enantiomer of the bioisostere of S3-G1A or S3-G1B, a racemic mixture of enantiomers of the bioisostere of S3-G1A or S3-G1B, and a pharmaceutically acceptable salt of the bioisostere of S3-G1A or S3-G1B, and wherein the bioisostere of S3-G1A or S3-G1B is selected from the group consisting of one of the following compounds:

| Compound Structure | IUPAC Name |
|---|---|
| 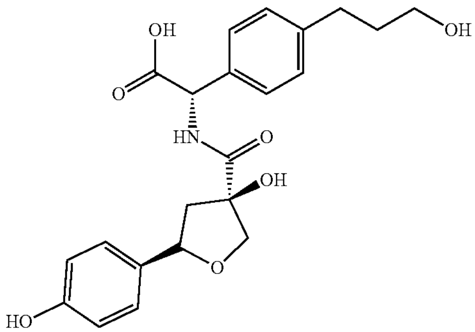 | (S)-2-((3R,5S)-3-hydroxy-5-(4-hydroxyphenyl)tetrahydrofuran-3-carboxamido)-2-(4-(3-hydroxypropyl)phenyl)acetic acid |
| 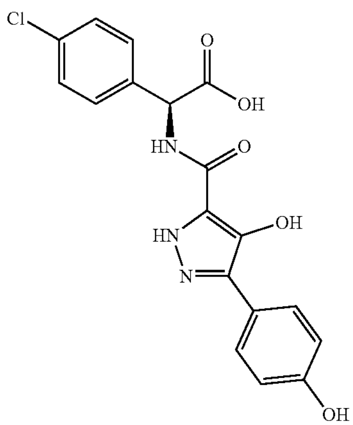 [SMILES: O=C(N[C@H](C(=O)O)c1ccc(Cl)cc1)c1[nH]nc(-c2ccc(O)cc2)c1O] | (S)-2-(4-chlorophenyl)-2-(4-hydroxy-3-(4-hydroxyphenyl)-1H-pyrazole-5-carboxamido)acetic acid |
| 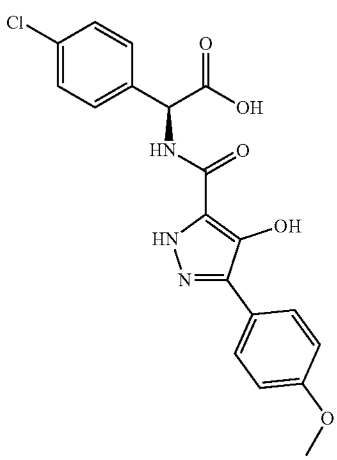 [SMILES: COc1ccc(-c2n[nH]c(C(=O)N[C@H](C(=O)O)c3ccc(Cl)cc3)c2O)cc1] | (S)-2-(4-chlorophenyl)-2-(4-hydroxy-3-(4-methoxyphenyl)-1H-pyrazole-5-carboxamido)acetic acid |
| 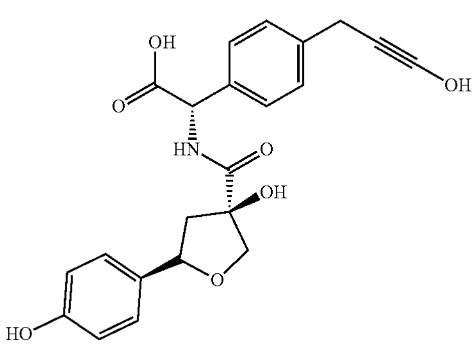 | (S)-2-((3R,5S)-3-hydroxy-5-(4-hydroxyphenyl)tetrahydrofuran-3-carboxamido)-2-(4-(3-hydroxyprop-2-yn-1-yl)phenyl)acetic acid. |

| Compound Structure | IUPAC Name |
|---|---|
| 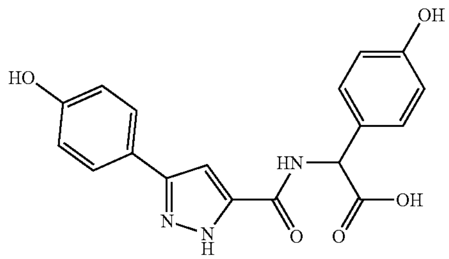 [SMILES: O=C(NC(C(=O)O)c1ccc(O)cc1)c1cc(-c2ccc(O)cc2)n[nH]1] | (S)-2-(4-hydroxyphenyl)-2-(3-(4 hydroxyphenyl)-1H-pyrazole-5-carboxamido)acetic acid |

In each of the foregoing embodiments, the bactericidal antibiotic can be selected from the group consisting of an aminoglycoside, an aminomethylcycline, an aminophenicol, an ansamycin, a β-lactam, a carbapenem, a dapsone, a 2,4-diaminopyrimidine, a glycopeptide, a glycycycline, a ketolid, a lincomycin, a lincosamide, a macrolide, a nitrofuran, an oxazolidinone, a peptide, a polymyxin, a quinolone, a rifabutin, a streptogramin, a sulfonamide, a sulfone, a tetracycline, and combinations thereof.

In each of the foregoing embodiments, the bactericidal antibiotic can be kanamycin, norfloxacin, or ampicillin.

In each of the foregoing embodiments, the pharmaceutical composition does not include enediyne antibiotics (e.g., calicheamicin, especially calicheamicin gamma II and calicheamicin omegaII) and/or antitumor antibiotics.

In each of the foregoing embodiments, the RelA enzyme inhibitor can be a compound selected from compounds of the Formulae I and II:

Ring (A) is a 6 membered ring selected from pyridine, pyrimidine, pyridazine, pyran, oxazine, thiazine, and piperazine; preferably Ring (A) is pyrimidine;

Ring (B) is a 6 membered ring selected from pyridine, pyrimidine, pyridazine, oxazine, or thiazine, $Z^1$ is a ring member of Ring (B) and $Z^1$ is nitrogen or a carbon substituted with hydrogen, cyano, amino or $C_{1-3}$ alkyl, ⚌ is a single bond, double bond or a bond in the aromatic ring, wherein $R^3$ and $R^4$ are substituents on ring carbon atoms and are each individually selected from hydrogen, cyano (—CN), amino (—NH$_2$) or $C_{1-3}$ alkyl; preferably Ring (B) is pyridine, $Z^1$ is a carbon substituted with hydrogen, $R^3$ is a cyano and $R^4$ is an amino; and Ring (C) is a 5 membered ring selected from oxazole, isoxazole, thiazole, pyrazole, imidazole, thiophene, pyrole, furan, tetrahydrofuran, tetrahydrothiophene, and pyrrolidine; preferably Ring (C) is pyrazole or tetrahydrofuran;

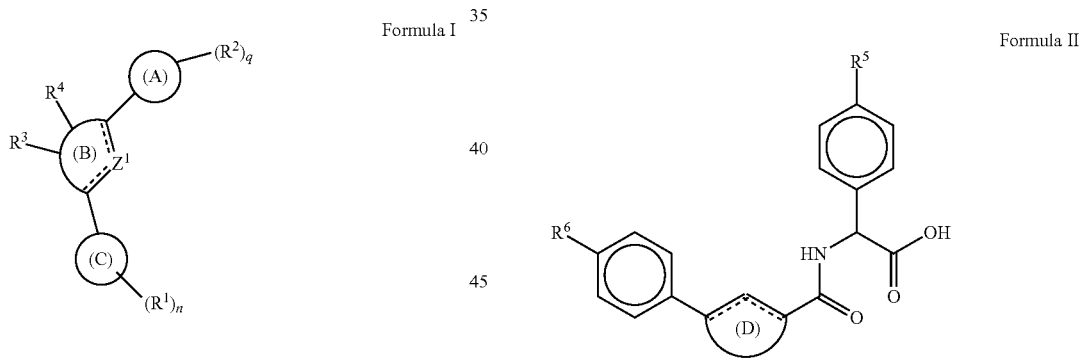

in Formula I, Ring (A) and Ring (C) are each bonded to carbon atoms of Ring (B) meta to one another;

n is 1 or 2, q is 1 or 2, $R^1$ and $R^2$ are each individually selected from the group consisting of hydrogen, carboxylic acid (—COOH), carboxylic $C_{1-6}$ alkyl ester, hydroxyl, cyano, nitro, amino, $C_{1-6}$ alkyl amino, amino $C_{1-6}$ alkyl, optionally substituted $C_{2-6}$ alkene, optionally substituted $C_{1-6}$ alkyl, optionally substituted $C_{3-8}$ cycloalkyl, optionally substituted $C_{1-6}$ alkoxy, optionally substituted $C_{2-10}$ heterocyclyl, and optionally substituted $C_{6-10}$ aromatic hydrocarbon, wherein the optional substituent(s) are each individually selected from carboxylic acid, carboxylic $C_{1-3}$ alkyl ester, $C_{1-6}$ alkyl, halogen, $C_{1-6}$ alkoxy, hydroxyl, amino, $C_{1-6}$ alkyl amino and amino $C_{1-6}$ alkyl; preferably n is 1, q is 1, $R^1$ is selected from the group consisting of hydrogen, carboxylic acid, and carboxylic $C_{1-6}$ alkyl ester; and $R^2$ is selected from the group consisting of hydrogen, amino, $C_{1-6}$ alkyl amino and amino $C_{1-6}$ alkyl;

in Formula II, Ring (D) is substituted at a first ring carbon with phenyl-$R^6$ and Ring (D) is substituted at a second ring carbon with the carbonyl of the amide group, and wherein the first ring carbon and the second ring carbon are each bonded to the same third ring carbon of Ring (D), $R^5$ is selected from the group consisting of hydrogen, carboxylic acid, carboxylic $C_{1-6}$ alkyl ester, halogen (such as F, Cl or Br), cyano, nitro, hydroxyl, amino, amino $C_{1-6}$ alkyl, $C_{1-6}$ alkyl amino, optionally substituted $C_{2-6}$ alkene, optionally substituted $C_{1-6}$ alkyl, optionally substituted $C_{3-6}$ alkyne, optionally substituted $C_{3-8}$ cycloalkyl, optionally substituted $C_{1-6}$ alkoxy, optionally substituted $C_{2-10}$ heterocyclyl, and optionally substituted $C_{6-10}$ aromatic hydrocarbon, wherein the optional substituent(s) are each individually selected from carboxylic acid, carboxylic $C_{1-3}$ ester, $C_{1-6}$ alkyl, halogen, $C_{1-6}$ alkoxy, hydroxyl, amino, $C_{1-6}$ alkyl amino, and amino $C_{1-6}$ alkyl; preferably $R^5$ is halogen, hydroxyl, $C_{3-6}$ alkyne which is optionally substituted with hydroxyl (such as (—CH$_2$—C≡C—OH)), or C$_{1-6}$ alkyl which is optionally substituted with hydroxyl;

R$^6$ is selected from the group consisting of hydrogen, carboxylic acid, carboxylic C$_{1-6}$ alkyl ester, cyano, nitro, hydroxyl, amino, amino C$_{1-6}$ alkyl, C$_{1-6}$ alkyl amino, optionally substituted C$_{2-6}$ alkene, optionally substituted C$_{1-6}$ alkyl, optionally substituted C$_{3-8}$ cycloalkyl, optionally substituted C$_{1-6}$ alkoxy (such as —OCH$_3$), optionally substituted C$_{2-10}$ heterocyclyl, and optionally substituted C$_{6-10}$ aromatic hydrocarbon, wherein the optional substituent(s) are each individually selected from carboxylic acid, carboxylic C$_{1-3}$ ester, C$_{1-6}$ alkyl, halogen, C$_{1-6}$ alkoxy, hydroxyl, amino, C$_{1-6}$ alkyl amino, and amino C$_{1-6}$ alkyl; preferably R$^6$ is C$_{1-6}$ alkoxy or hydroxyl; and Ring (D) is an optionally substituted 5-membered heterocycle selected from oxazole, isoxazole, thiazole, pyrazole, imidazole, thiophene, pyrole, furan, tetrahydrofuran, tetrahydrothiophene, and pyrrolidine, wherein the optional substituent(s) are each individually selected from hydrogen, carboxylic acid, carboxylic C$_{1-3}$ ester, C$_{1-6}$ alkyl, halogen, C$_{1-6}$ alkoxy, hydroxyl, amino, C$_{1-6}$ alkyl amino, and amino C$_{1-6}$ alkyl; ⎓ is a single bond, double bond or a bond in the aromatic ring; preferably Ring (D) is pyrazole or tetrahydrofuran and Ring (D) is optionally substituted with a hydroxyl;enantiomers of the compounds of the formulae I and II, and pharmaceutically acceptable salts of any of the foregoing compounds.

In an aspect, the present invention provides a method of treating a bacterial biofilm disease in a patient comprising administering to said patient an effective amount of the composition of any one of the foregoing embodiments.

In an aspect, the present invention provides a method of inhibiting a RelA enzyme in bacteria in the presence of a bactericidal antibiotic, comprising contacting a RelA enzyme with the RelA enzyme inhibitor of any one of the foregoing embodiments.

In each of the foregoing embodiments, the bacterial biofilm disease can be selected from chronic otitis media with effusion, otorrhea, chronic pharyngitis, chronic sinusitis, chronic tonsillitis, cholesteatoma, native and artificial valve endocarditis, chronic obstructive pulmonary disease (COPD), cystic fibrosis pneumonias, bacterial vaginosis, pelvic inflammatory disease, endometritis, salpingitis, chronic prostatitis, periodontal disease, neuroborreliosis and other chronic bacterial infections of the central nervous system, septic arthritis, bony non-unions, infected catheters, infected arthroplasties, other infected implanted medical devices including pace makers, screws, plates, stents, grafts, wounds, chronic non-healing wounds including pressure ulcers, diabetic ulcers, burns, decubitus ulcers, chronic pelvic pain syndromes, and lower back pain associated with biofilm infections in the nucleus polposa of the vertebral disks; or the bacterial biofilm disease is selected from chronic otitis media with effusion, neuroborreliosis, and lower back pain associated with biofilm infections in the nucleus polposa of the vertebral disks; or the bacterial biofilm disease is selected from chronic otitis media with effusion and neuroborreliosis.

In each of the foregoing embodiments, the patient can be a mammal; or the patient can be a human, horse, dog or cat; or the patient can be a human.

In each of the foregoing embodiments, the pharmaceutical composition can be administered subcutaneously, orally, intravenously, or topically; or the pharmaceutical composition is administered subcutaneously, orally, or topically; or the pharmaceutical composition is administered subcutaneously or topically.

In an aspect, the present invention provides a RelA enzyme inhibitor that binds to RelA enzyme with a predicted binding score which is less than or equal to −9 kcal/mole; or a predicted binding score which is less than −9.5 kcal/mole; or a predicted binding score which is −13.57 to −9.5 kcal/mole, and is selected from the group consisting of a compound of formulae I and II:

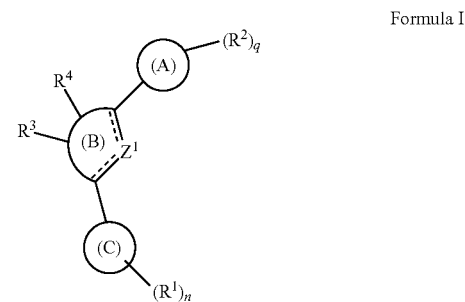

Formula I in Formula I, Ring (A) and Ring (C) are each bonded to carbon atoms of Ring (B) meta to one another;

n is 1 or 2, q is 1 or 2,

R$^1$ and R$^2$ are each individually selected from the group consisting of hydrogen, carboxylic acid, carboxylic C$_{1-6}$ alkyl ester, hydroxyl, cyano, nitro, amino, C$_{1-6}$ alkyl amino, amino C$_{1-6}$ alkyl, optionally substituted C$_{2-6}$ alkene, optionally substituted C$_{1-6}$ alkyl, optionally substituted C$_{3-8}$ cycloalkyl, optionally substituted C$_{1-6}$ alkoxy, optionally substituted C$_{2-10}$ heterocyclyl, and optionally substituted C$_{6-10}$ aromatic hydrocarbon, wherein the optional substituent(s) are each individually selected from carboxylic acid, carboxylic C$_{1-3}$ alkyl ester, C$_{1-6}$ alkyl, halogen, C$_{1-6}$ alkoxy, hydroxyl, amino, C$_{1-6}$ alkyl amino and amino C$_{1-6}$ alkyl; preferably n is 1, q is 1, R$^1$ is selected from the group consisting of hydrogen, carboxylic acid, and carboxylic C$_{1-6}$ alkyl ester; and R$^2$ is selected from the group consisting of hydrogen, amino, C$_{1-6}$ alkyl amino and amino C$_{1-6}$ alkyl;

Ring (A) is a 6 membered ring selected from pyridine, pyrimidine, pyridazine, pyran, oxazine, thiazine, and piperazine; preferably Ring (A) is pyrimidine;

Ring (B) is a 6 membered ring selected from pyridine, pyrimidine, pyridazine, oxazine, or thiazine, Z$^1$ is a ring member of Ring (B) and Z$^1$ is nitrogen or a carbon substituted with hydrogen, cyano, amino or C$_{1-3}$ alkyl, ⎓ is a single bond, double bond or a bond in the aromatic ring, wherein R$^3$ and R$^4$ are substituents on ring carbon atoms and are each individually selected from hydrogen, cyano, amino or C$_{1-3}$ alkyl; preferably Ring (B) is pyridine, Z$^1$ is a carbon substituted with hydrogen, R$^3$ is a cyano and R$^4$ is an amino; and Ring (C) is a 5 membered ring selected from oxazole, isoxazole, thiazole, pyrazole, imidazole, thiophene, pyrole, furan, tetrahydrofuran, tetrahydrothiophene, and pyrrolidine; preferably Ring (C) is pyrazole or tetrahydrofuran;

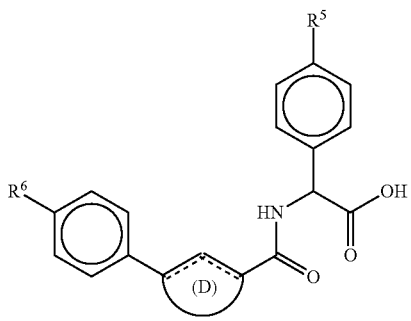

Formula II in Formula II, Ring (D) is substituted at a first ring carbon with phenyl-$R^6$ and Ring (D) is substituted at a second ring carbon with the carbonyl of the amide group, and wherein the first ring carbon and the second ring carbon are each bonded to the same third ring carbon of Ring (D), $R^5$ is selected from the group consisting of hydrogen, carboxylic acid, carboxylic $C_{1-6}$ alkyl ester, halogen, cyano, nitro, hydroxyl, amino, amino $C_{1-6}$ alkyl, $C_{1-6}$ alkyl amino, optionally substituted $C_{2-6}$ alkene, optionally substituted $C_{1-6}$ alkyl, optionally substituted $C_{3-6}$ alkyne, optionally substituted $C_{3-8}$ cycloalkyl, optionally substituted $C_{1-6}$ alkoxy, optionally substituted $C_{2-10}$ heterocyclyl, and optionally substituted $C_{6-10}$ aromatic hydrocarbon, wherein the optional substituent(s) are each individually selected from carboxylic acid, carboxylic $C_{1-3}$ ester, $C_{1-6}$ alkyl, halogen, $C_{1-6}$ alkoxy, hydroxyl, amino, $C_{1-6}$ alkyl amino, and amino $C_{1-6}$ alkyl; preferably $R^5$ is halogen, hydroxyl, $C_{3-6}$ alkyne which is optionally substituted with hydroxyl, or $C_{1-6}$ alkyl which is optionally substituted with hydroxyl;

$R^6$ is selected from the group consisting of hydrogen, carboxylic acid, carboxylic $C_{1-6}$ alkyl ester, cyano, nitro, hydroxyl, amino, amino $C_{1-6}$ alkyl, $C_{1-6}$ alkyl amino, optionally substituted $C_{2-6}$ alkene, optionally substituted $C_{1-6}$ alkyl, optionally substituted $C_{3-8}$ cycloalkyl, optionally substituted $C_{1-6}$ alkoxy, optionally substituted $C_{2-10}$ heterocyclyl, and optionally substituted $C_{6-10}$ aromatic hydrocarbon, wherein the optional substituent(s) are each individually selected from carboxylic acid, carboxylic $C_{1-3}$ ester, $C_{1-6}$ alkyl, halogen, $C_{1-6}$ alkoxy, hydroxyl, amino, $C_{1-6}$ alkyl amino, and amino $C_{1-6}$ alkyl; preferably $R^6$ is $C_{1-6}$ alkoxy or hydroxyl; and Ring (D) is an optionally substituted 5-membered heterocycle selected from oxazole, isoxazole, thiazole, pyrazole, imidazole, thiophene, pyrole, furan, tetrahydrofuran, tetrahydrothiophene, and pyrrolidine, wherein the optional substituent(s) are each individually selected from hydrogen, carboxylic acid, carboxylic $C_{1-3}$ ester, $C_{1-6}$ alkyl, halogen, $C_{1-6}$ alkoxy, hydroxyl, amino, $C_{1-6}$ alkyl amino, and amino $C_{1-6}$ alkyl; ⸺ is a single bond, double bond or a bond in the aromatic ring; preferably Ring (D) is pyrazole or tetrahydrofuran and Ring (D) is optionally substituted with a hydroxyl; an enantiomer of a compound of the formulae I and II, and a pharmaceutically acceptable salt of a compound of the formulae I and II, with the proviso that (4-chlorophenyl)([(3-(4-hydroxyphenyl)-1H-pyrazol-5-yl]carbonyl)amino)acetic acid and 3-(6-amino-5-cyano-4-[2-(propylamino)pyrimidin-5-yl]pyridin-2-yl))-1H-pyrazole-5-carboxylic acid are excluded.

In each of the foregoing embodiments, the RelA enzyme inhibitor can be selected from the group consisting of one of the following compounds, an enantiomer of one of the following compounds, a racemic mixture of one of the following compounds and a pharmaceutically acceptable salt of any of the foregoing compounds and mixtures:

| Compound Structure | IUPAC Name |
|---|---|
| ![structure] | (S)-2-((3R,5S)-3-hydroxy-5-(4-hydroxyphenyl)tetrahydrofuran-3-carboxamido)-2-(4-(3-hydroxypropyl)phenyl)acetic acid |
| ![structure] | (S)-2-(4-chlorophenyl)-2-(4-hydroxy-3-(4-hydroxyphenyl)-1H-pyrazole-5-carboxamido)acetic acid |

| Compound Structure | IUPAC Name |
|---|---|
| 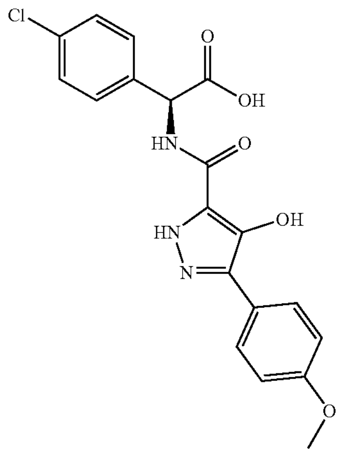 [SMILES: COc1ccc(-c2n[nH]c(C(=O)N[C@H](C(=O)O)c3ccc(Cl)cc3)c2O)cc1] | (S)-2-(4-chlorophenyl)-2-(4-hydroxy-3-(4-methoxyphenyl)-1H-pyrazole-5-carboxamido)acetic acid |
| 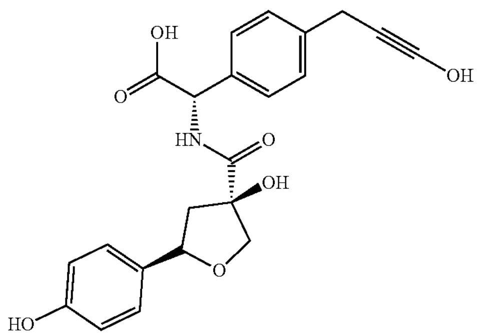 | (S)-2-((3R,5S)-3-hydroxy-5-(4-hydroxyphenyl)tetrahydrofuran-3-carboxamido)-2-(4-(3-hydroxyprop-2-yn-1-yl)phenyl)acetic acid. |
| 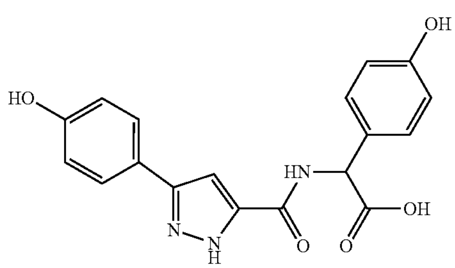 [SMILES: O=C(NC(C(=O)O)c1ccc(O)cc1)c1cc(-c2ccc(O)cc2)n[nH]1] | (S)-2-(4-hydroxyphenyl)-2-(3-(4-hydroxyphenyl)-1H-pyrazole-5-carboxamido)acetic acid |

In an aspect, the present invention provides a process of preparing 2-(4-chlorophenyl)-2-(3-(4-hydroxyphenyl)-1H-pyrazole-5-carboxamido)acetic acid comprising steps of:

protecting the carboxylic acid of the following compound, an enantiomer or racemic mixture thereof with a protecting group:

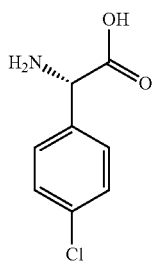

combining the protected compound with:

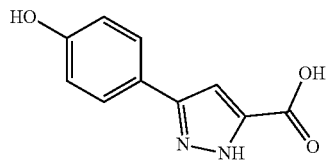 [SMILES: O=C(O)c1cc(-c2ccc(O)cc2)n[nH]1]

and removing the protecting group.

In each of the foregoing embodiments, methanol can be used to form the protecting group.

In each of the foregoing embodiments, the process of forming 2-(4-chlorophenyl)-2-(3-(4-hydroxyphenyl)-1H-pyrazole-5-carboxamido)acetic acid can be as follows:

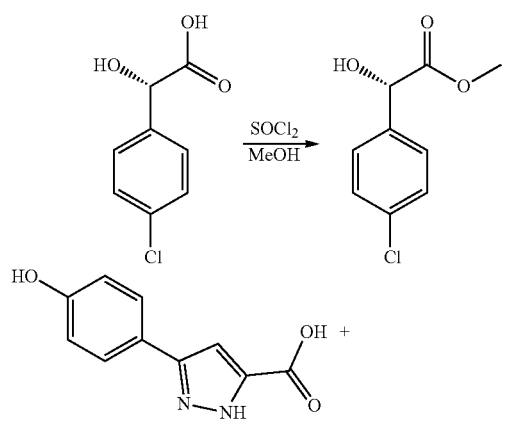

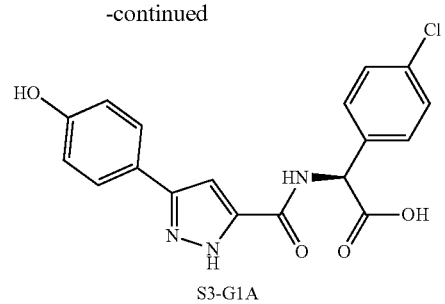

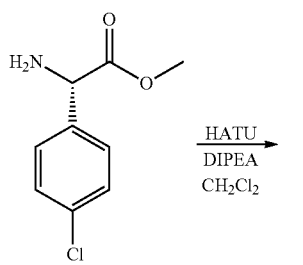

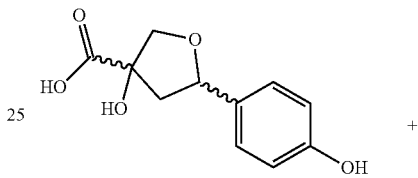

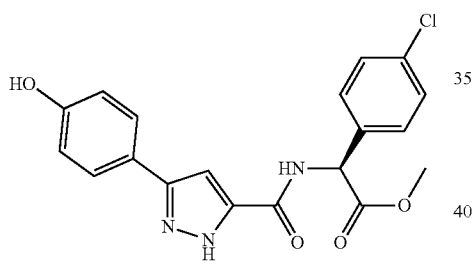

In an aspect, the present invention provides a process of forming 2-((3,5)-3-hydroxy-5-(4-hydroxyphenyl)tetrahydrofuran-3-carboxamido)-2-(4-(3-hydroxypropyl)phenyl)acetic acid comprises the steps of:

combining (a) and (b)

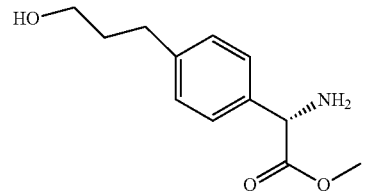

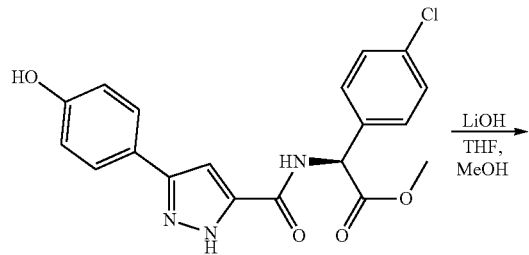

wherein the methyl group protecting the carboxylic acid of (b) can be any protecting group, and deprotecting the carboxylic acid.

In each of the foregoing embodiments, the process of forming 2-((3,5)-3-hydroxy-5-(4-hydroxyphenyl)tetrahydrofuran-3-carboxamido)-2-(4-(3-hydroxypropyl)phenyl)acetic acid can comprise:

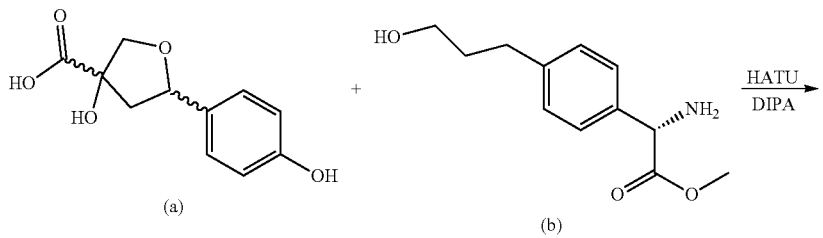

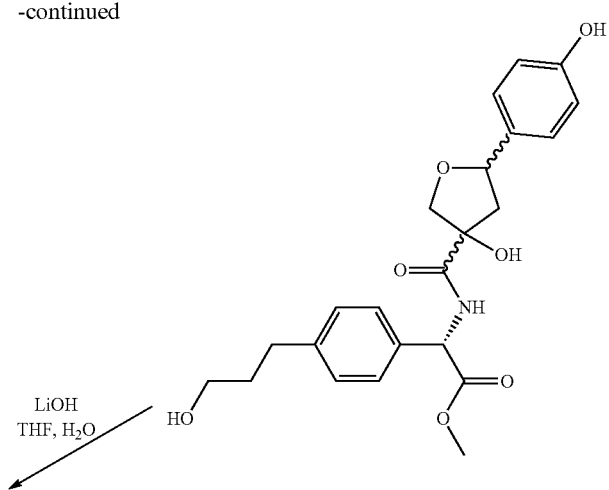

LiOH
THF, H₂O

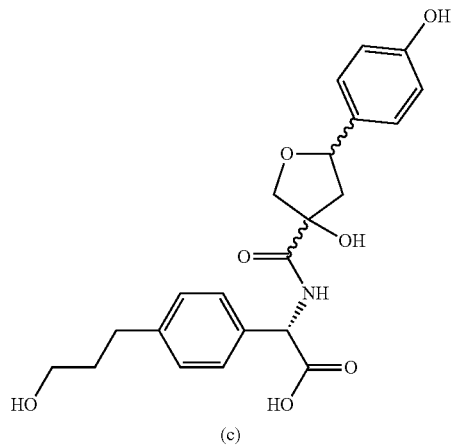

(c)

In each of the foregoing embodiments, the process of forming 2-((3,5)-3-hydroxy-5-(4-hydroxyphenyl)tetrahydrofuran-3-carboxamido)-2-(4-(3-hydroxypropyl)phenyl)acetic acid can further comprise a step wherein (a) is formed by reacting an alkaline or alkaline earth peroxide with

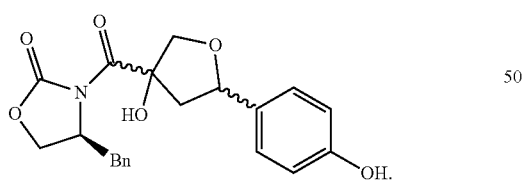

In each of the foregoing embodiments, the process of forming 2-((3,5)-3-hydroxy-5-(4-hydroxyphenyl)tetrahydrofuran-3-carboxamido)-2-(4-(3-hydroxypropyl)phenyl)acetic acid can further comprise the following steps wherein (a) is formed:

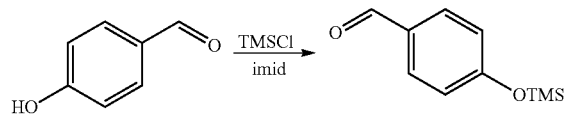

-continued
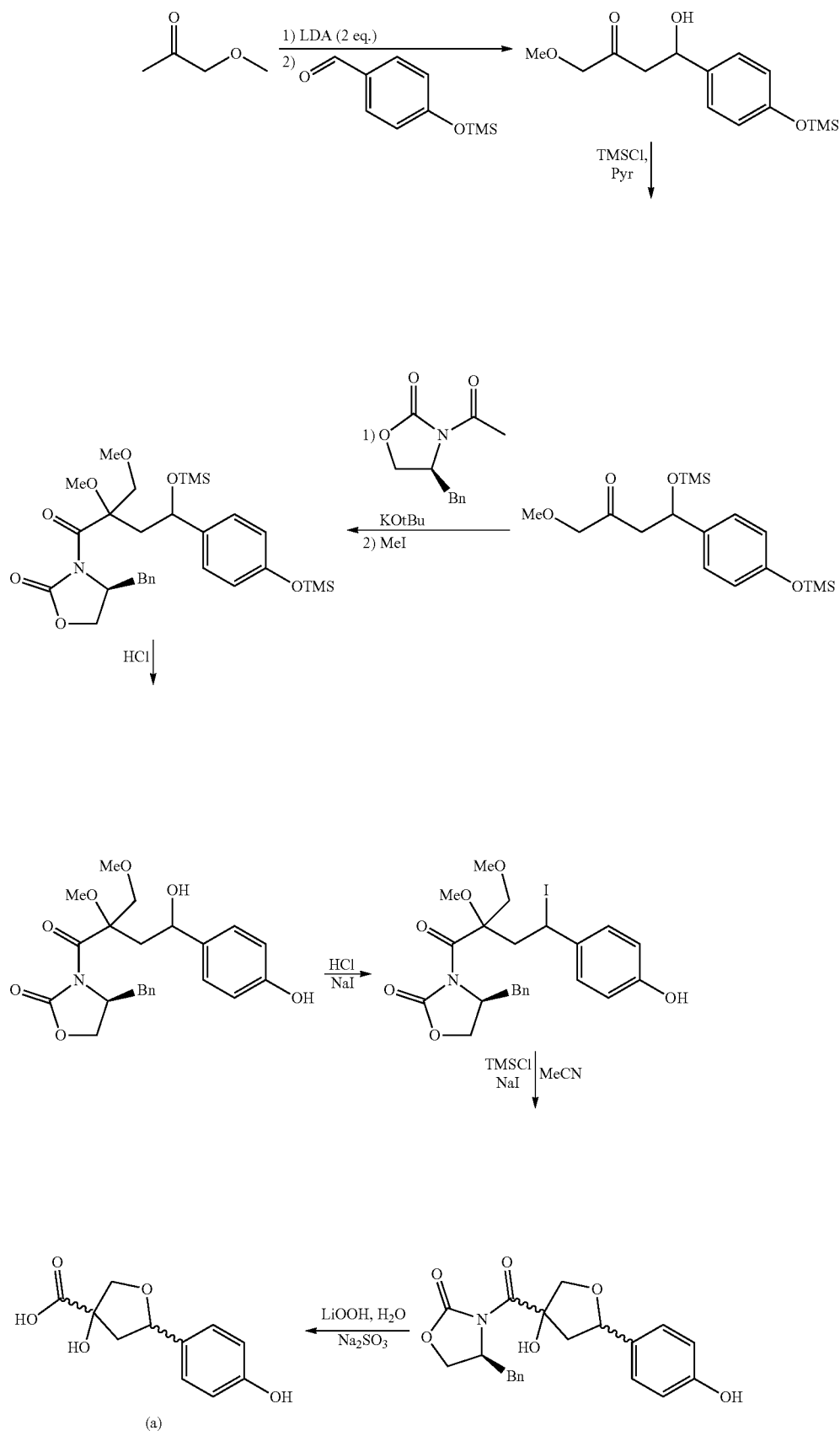

In each of the foregoing embodiments, the process of forming 2-((3,5)-3-hydroxy-5-(4-hydroxyphenyl)tetrahydrofuran-3-carboxamido)-2-(4-(3-hydroxypropyl)phenyl) acetic acid can further comprise the following steps wherein (b) is formed:

protecting the amine group in the following compound

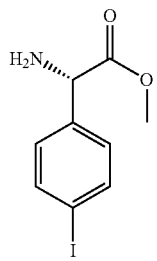

with a protecting group,
replacing the iodo group with a 3 hydroxypropyl group, and
deprotecting the amine group.

In each of the foregoing embodiments, the process of forming 2-((3,5)-3-hydroxy-5-(4-hydroxyphenyl)tetrahydrofuran-3-carboxamido)-2-(4-(3-hydroxypropyl)phenyl) acetic acid can further comprise the following steps wherein (b) is formed:

In each of the foregoing embodiments, the $C_{6-10}$ aromatic hydrocarbon can be phenyl or naphthalene.

In each of the foregoing embodiments, the halogen is can be fluoro, chloro, bromo or iodo.

In each of the foregoing embodiments, the transitional phrase can be replaced with the terms "consisting essentially of". The transitional phrase "consisting essentially of" limits the scope of a claim/embodiment(s) to the specified materials or steps and those that do not materially affect the basic and novel characteristics of the claimed invention/embodiment(s). Herein, the basic and novel characteristics of the claimed invention/embodiment(s) include the pharmaceutical acceptability of the composition and the ability of the composition to treat bacterial biofilm diseases.

In each of the foregoing embodiments, the transitional phrase can be replaced with the terms "consisting of". The transitional phrase "consisting of" excludes any element, step, or ingredient not specified in the claim/embodiment(s).

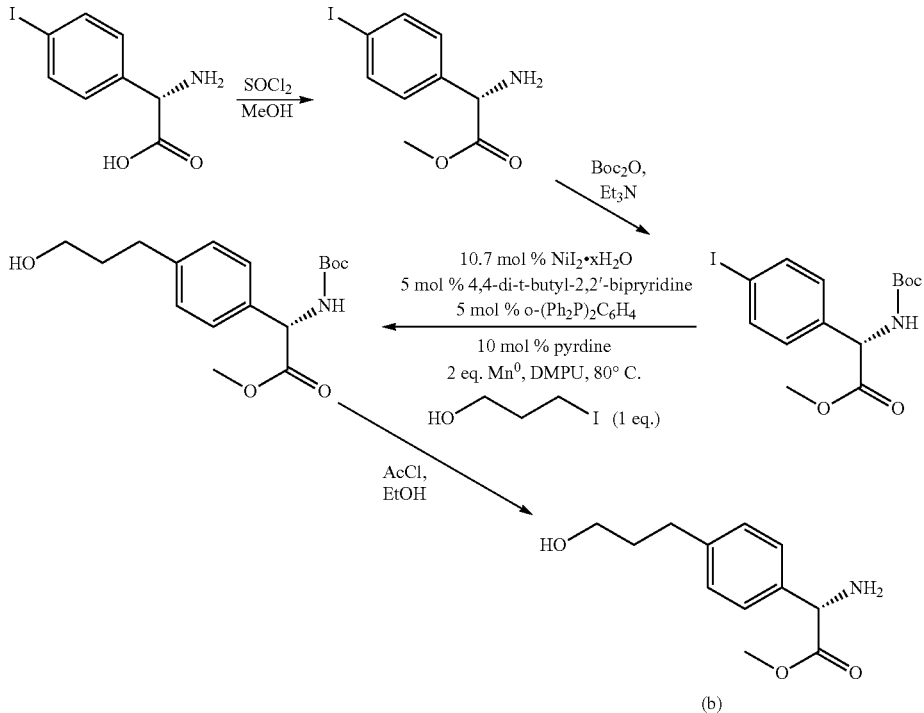

In each of the foregoing embodiments, the $C_{2-10}$ heterocyclyl can be pyridine, pyrimidine, pyridazine, pyran, oxazine, thiazine, piperazine, oxazole, isoxazole, thiazole, pyrazole, imidazole, thiophene, pyrole, furan, tetrahydrofuran, tetrahydrothiophene, pyrrolidine, azetidine, piperidine, tetrahydropyridine, morpholine, 1,1-dioxidothiomorpholine, oxetane, 3-azabicyclo[2.2.1]heptane, 3-azabicyclo[3.3.1]nonane, or 7-azaspiro[3.5]nonane.

Figure 3:
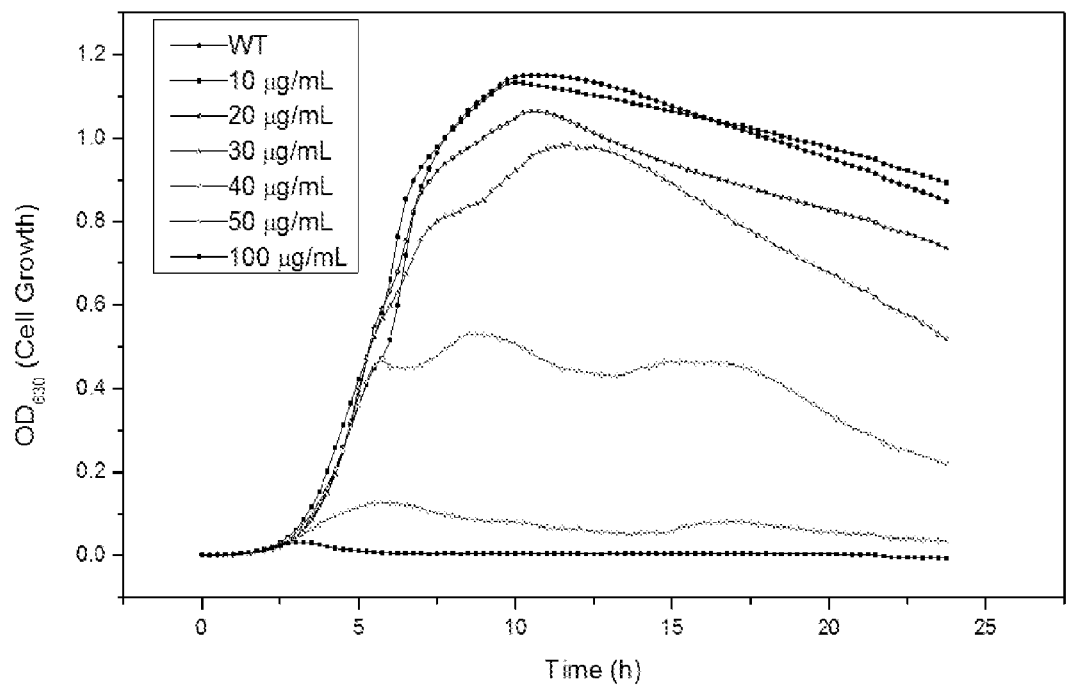

FIGS. 3 show the effect of different ampicillin concentrations on planktonic growth of *E. coli* C.

Figure 4:
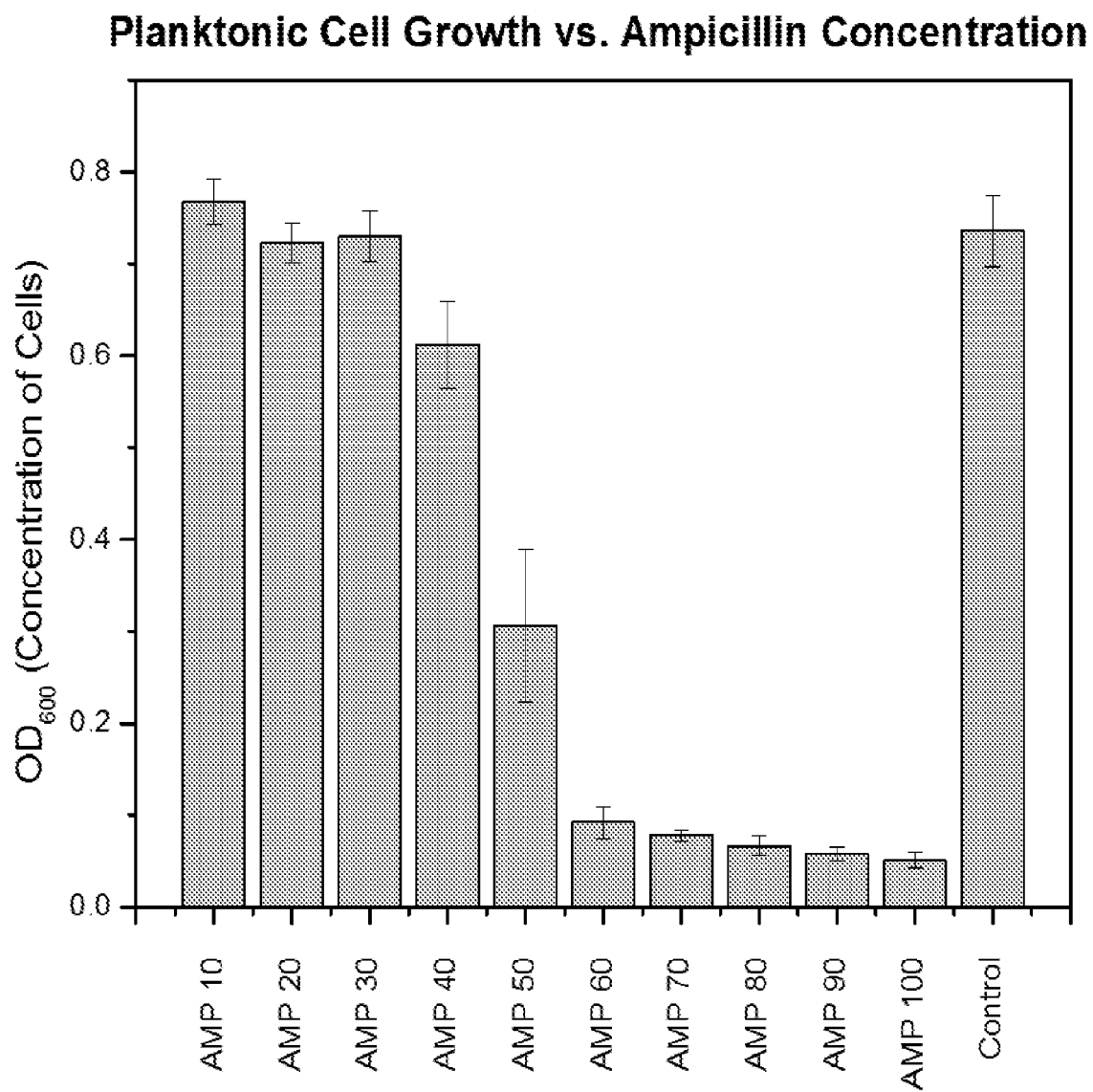

FIG. 4 shows the effect of different ampicillin concentrations on *E. coli* C cells in biofilm. Amp #=Ampicillin μg/mL.

FIG. 5 shows the effect of the compounds on *E. coli* C biofilm formation (a) cell densities, and (b) biofilm amount (crystal violet). A=S1-G1A, B=S1-G1B, SH=serine hydroxamate, and IDR=IDR-1018.

Figure 6:
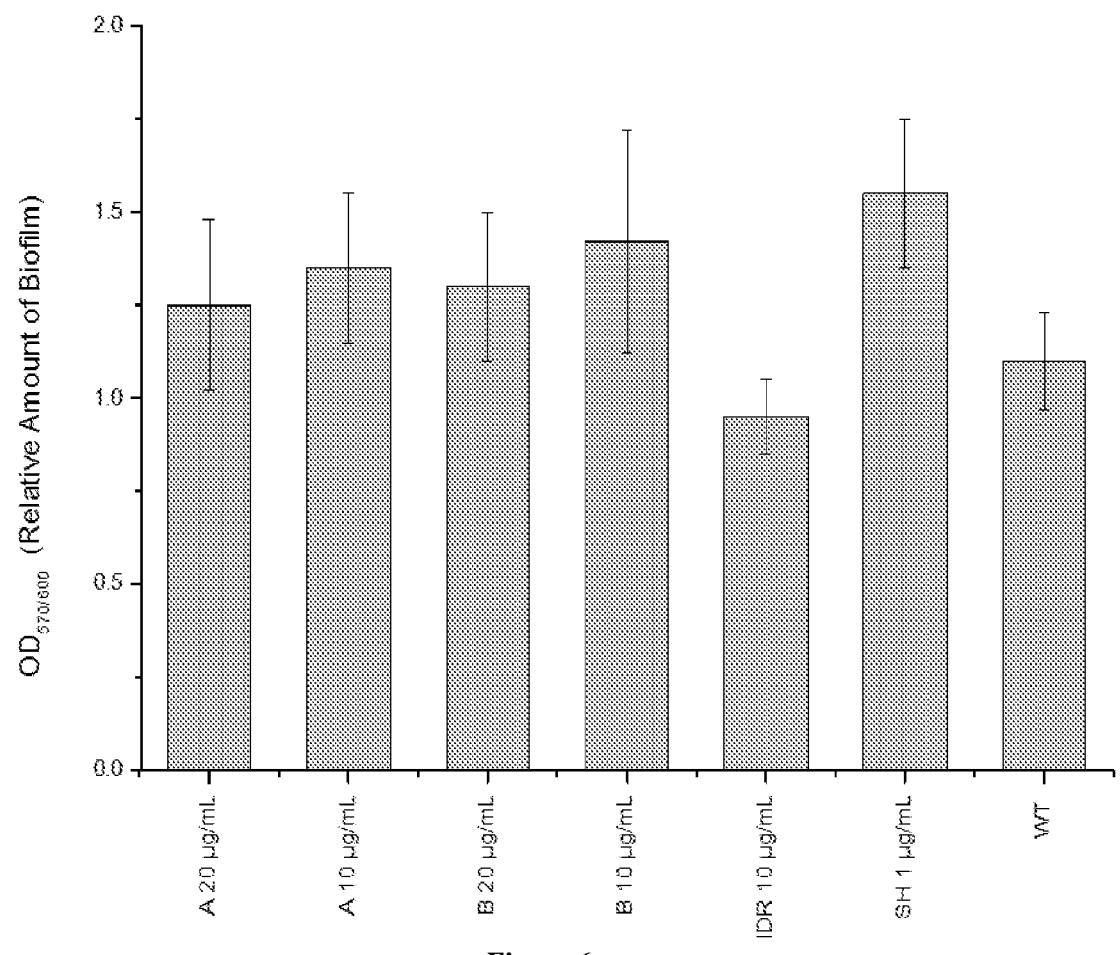

FIGS. 6 show the effect of small molecule RelA enzyme inhibitors on biofilm persistence.

Figure 7:
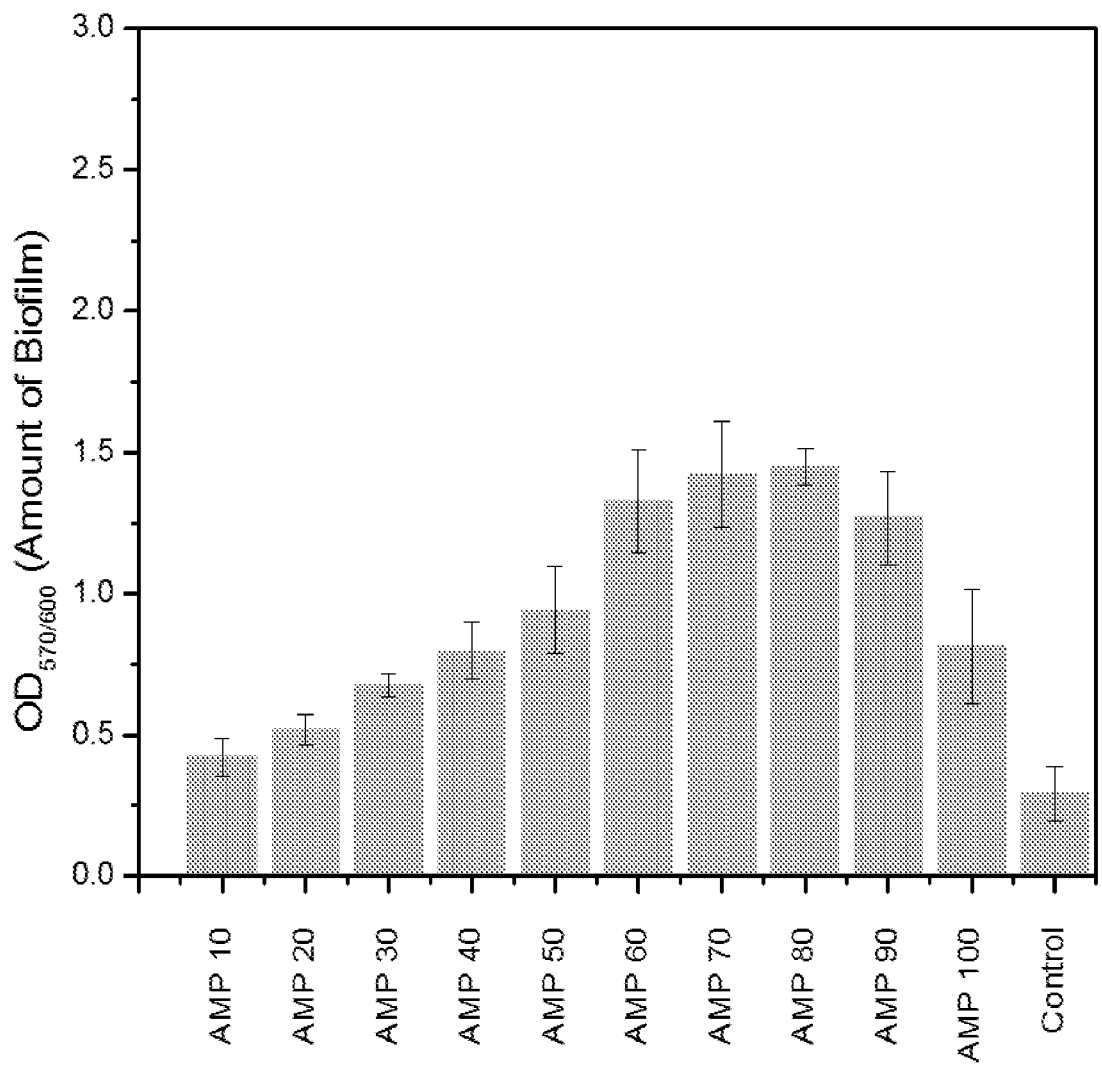

FIG. 7 shows the effect of ampicillin concentrations on *E. coli* C biofilm persistence.

Figure 8:
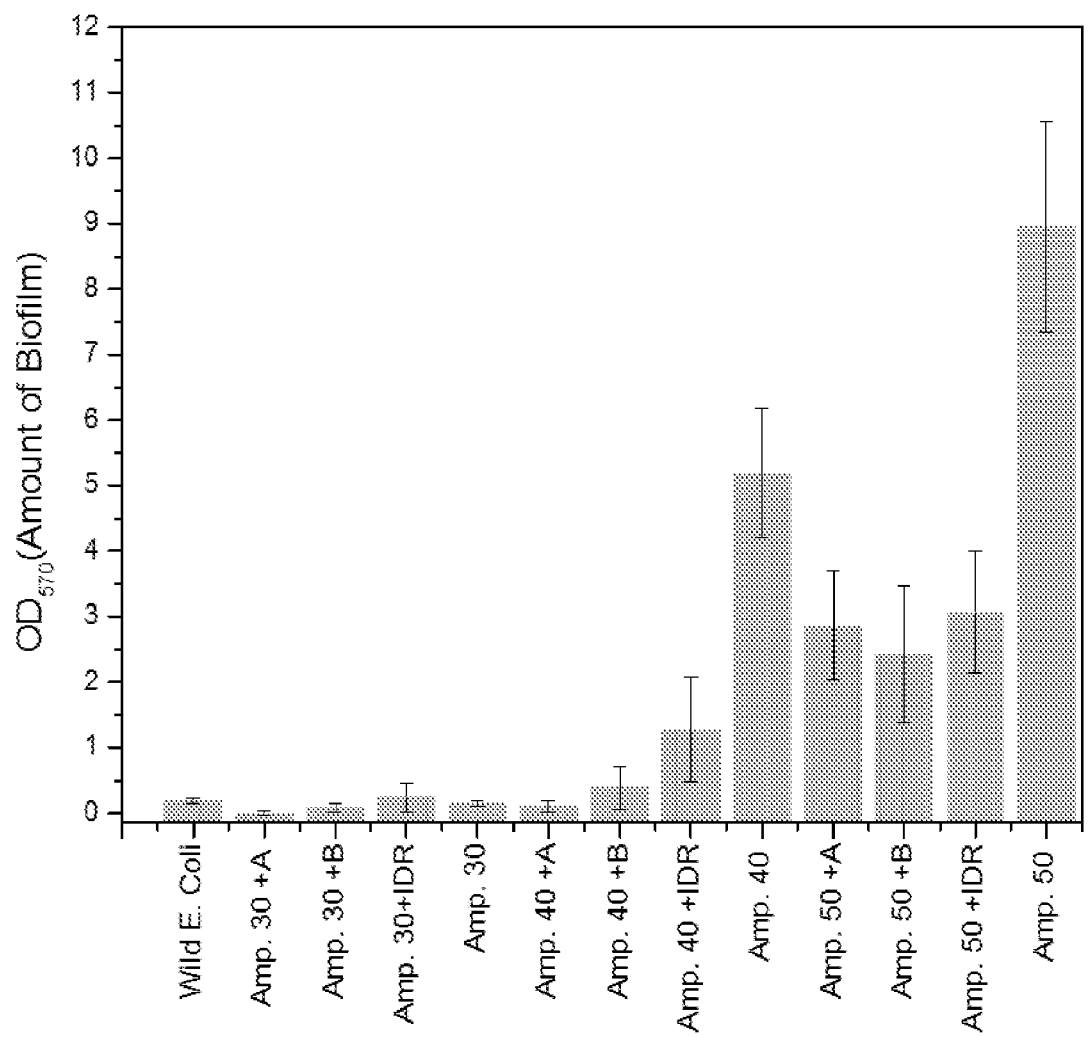

FIG. 8 shows the biofilm degradation utilizing compounds and ampicillin.

DEFINITIONS

In order to facilitate understanding of the examples provided herein, certain frequently occurring terms are defined herein.

In connection with a measured quantity, the term "about" as used herein refers to the normal variation in that measured quantity that would be expected by a skilled person making the measurement and exercising a level of care commensurate with the objective of the measurement and the precision of the measuring equipment used. Unless otherwise indicated, "about" refers to a variation of +/−10% of the value provided.

A "biofilm" as used herein refers to a structured consortium of bacteria embedded in a self-produced polymer matrix consisting of polysaccharide, protein and DNA (HØiby et al., *International Journal of Antimicrobial Agents* 2010, 35 (4), 322-332). This matrix is called the EPS (extracellular polymeric substance). This EPS can protect the biofilm excreting bacteria colonies from outside stresses. The combination of lowered metabolic rate and upregulation of protective enzymes in biofilms collectively make biofilm infections antibiotic resistant.

A "stringent response" as used herein refers to a systematic reaction to stresses placed on a cell or group of cells. The stresses that are often associated with the stringent response include starvation of essential amino acids, heat shock, iron limitation, population density, and oxidative stress (associated with antibiotic treatment) (Godfrey 2002; Brown 2016; Albesa 2004; and Kudrin 2017) This stringent response is pleiotropic and leads to antibiotic resistance and formation of bacteria biofilms.

A "bioisostere" is a molecule resulting from the exchange of an atom or of a group of atoms with an alternative, broadly similar, atom or group of atoms. The objective of a bioisosteric replacement is to create a new molecule with similar biological properties to the parent compound.

An "enantiomer" is also known as an optical isomer and is one of two stereoisomers that are mirror images of each other that are non-superimposable (not identical).

A "racemic mixture", or racemate is one that has equal amounts of left- and right-handed enantiomers of a chiral molecule.

"Stereoisomers" are isomeric molecules that have the same molecular formula and sequence of bonded atoms (constitution) but differ in the three-dimensional orientations of their atoms in space.

As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art. Methods for selection and production of appropriate prodrug derivative can be found, for example, in Design of Prodrugs, Elsevier, Amsterdam 1985.

The term "effective amount" of an agent as used herein, e.g., a pharmaceutical formulation, refers to an amount effective, at dosages and for periods of time necessary, to achieve a desired therapeutic or prophylactic result.

The term "individual" or "subject" or "patient" as used herein refers to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject or patient is a human.

The term "pharmaceutical formulation" as used herein refers to a preparation which is in such form as to permit the biological activity of an active ingredient contained therein to be effective, and which contains no additional components which are unacceptably toxic to a subject to which the formulation would be administered.

The term "pharmaceutically acceptable carrier" as used herein refers to an ingredient in a pharmaceutical formulation, other than an active ingredient, which is nontoxic to a subject. A pharmaceutically acceptable carrier includes, but is not limited to a buffer, excipient, stabilizer, or preservative.

The term "therapeutically effective amount" of the RelA inhibitor and the bactericidal antibiotic of the invention means a sufficient amount of the RelA inhibitor and the bactericidal antibiotic to treat the infection, at a reasonable benefit/risk ratio applicable to any medical treatment. It will be understood, however, that the total daily usage of the RelA inhibitor and the bactericidal antibiotic and compositions of the present invention will be decided by the attending physician within the scope of sound medical judgment. The specific therapeutically effective dose level for any particular patient will depend upon a variety of factors including the infection being treated and the severity of the infection; activity of the bactericidal antibiotic employed; the specific composition employed, the age, body weight, general health, sex and diet of the patient; the time of administration, route of administration, the duration of the treatment; drugs used in combination or coincidental with the specific RelA inhibitor and the bactericidal antibiotic employed; and like factors well known in the medical arts. For example, it is well known within the skill of the art to start doses of the compound at levels lower than those required to achieve the desired therapeutic effect and to gradually increase the dosage until the desired effect is achieved.

The term "treatment," "treat," or "treating" as used herein refers to clinical intervention in an attempt to alter the natural course of the individual being treated and can be performed either for prophylaxis or during the course of clinical pathology. Desirable effects of treatment include, but are not limited to, preventing occurrence or recurrence of bacterial infection, alleviation of symptoms, diminishment of any direct or indirect pathological consequences of the bacterial infection, decreasing the rate of bacterial infection progression, amelioration or palliation of the bacterial infection state, and remission or improved prognosis. In some embodiments, RelA inhibitor and the bactericidal antibiotic of the invention are used to delay development of a bacterial infection or to slow the progression of a bacterial infection.

DETAILED DESCRIPTION

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in, other systems and methods. Before explaining the disclosed embodiments of the present invention in detail, it is to be understood that the invention is not limited in its application to the details of any particular embodiment shown. Additionally, the terminology used herein is for the purpose of description and not for limitation. Furthermore, although certain methods are described with reference to steps that are presented herein in a certain order, in many instances, these steps can be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more", and "at least one" can be used interchangeably herein. The terms "comprising", "including", "having" and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent, or parameter disclosed herein is to be interpreted as being disclosed for use alone or in combination with one or more of each and every other component, compound, substituent, or parameter disclosed herein.

It is also to be understood that each amount/value or range of amounts/values for each component, compound, substituent, or parameter disclosed herein is to be interpreted as also being disclosed in combination with each amount/value or range of amounts/values disclosed for any other component(s), compounds(s), substituent(s), or parameter(s) disclosed herein and that any combination of amounts/values or ranges of amounts/values for two or more component(s), compounds(s), substituent(s), or parameters disclosed herein are thus also disclosed in combination with each other for the purposes of this description.

It is further understood that each lower limit of each range disclosed herein is to be interpreted as disclosed in combination with each upper limit of each range disclosed herein for the same component, compounds, substituent, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, substituent, or parameter disclosed in the description or an example is to be interpreted as a disclosure of either a lower or an upper limit of a range and thus can be combined with any other lower or upper limit of a range or specific amount/value for the same component, compound, substituent, or parameter disclosed elsewhere in the application to form a range for that component, compound, substituent, or parameter.

In an aspect, the present invention is drawn to a pharmaceutical composition comprising a RelA enzyme inhibitor and a bactericidal antibiotic, wherein said RelA enzyme inhibitor binds to RelA enzyme. Various forms of RelA enzyme inhibitors may be utilized including, but not limited to, the free base, or a salt. For instance, the RelA enzyme inhibitor may be in the form of a salt, and examples of such a salt include a pharmaceutically acceptable salt such as salts with inorganic bases, salts with organic bases, salts with inorganic acids, salts with organic acids, salts with basic or acidic amino acids, and the like. Preferable examples of the salts with inorganic bases include salts with alkali metals such as sodium, potassium, etc.; alkaline earth metals such as calcium, magnesium, etc.; aluminum; ammonium; and the like. Preferable examples of the salts with organic bases include salts with trimethylamine, triethylamine, pyridine, picoline, ethanolamine, diethanolamine, triethanolamine, dicyclohexylamine, N, N-dibenzylethylenediamine, etc. Preferable examples of the salts with inorganic acids include salts with hydrochloric acid, hydrobromic acid, nitric acid, sulfuric acid, phosphoric acid, etc. Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. Preferable examples of the salts with basic amino acids include salts with arginine, lysine, ornithine, etc., and preferable examples of the salts with acidic amino acids include salts with aspartic acid, glutamic acid, etc. In addition, the RelA enzyme inhibitors may be any of anhydrides and hydrates. The RelA enzyme inhibitor may also be present as a complex, a prodrug, an enantiomer, a racemic mixture or stereoisomers.

Bactericidal Antibiotics

A large variety of classes of antibiotics can be used according to the present invention. Exemplary structural classes of antibiotics include, but are not limited to, aminoglycosides, aminomethylcyclines, amphenicols, ansamycins, β-lactams (e.g., penicillins or cephalosporins), carbapenems, dapsones, 2,4-diaminopyrimidines, glycopeptides, glycycyclines, ketolides, lincomycins, lincosamides, macrolides, nitrofurans, oxazolidinones, peptides, polymyxins, quinolones, rifabutins, streptogramins, sulfonamides, sulfones, tetracyclines, and combinations thereof. A few examples of classes of antibiotics are described below.

Quinolone Antibiotics and Other Bacterial Type II Topoisomerase Inhibitors

Quinolone antibiotics are compounds that contain a quinolone or a naphthyridine nucleus with any of a variety of different side chains and substituents. Numerous modifications of the originally identified core structures have been made resulting in a large number of compounds with activity against differing groups of bacteria.

Quinolone antibiotics include, but are not limited to, any of the antibacterial agents disclosed in the foregoing references including, but not limited to, ciprofloxacin, oxolinic acid, cinoxacin, flumequine, miloxacin, rosoxacin, pipemidic acid, norfloxacin, enoxacin, moxifloxacin, gatifloxacin, ofloxacin, lomefloxacin, temafloxacin, fleroxacin, pefloxacin, amifloxacin, sparfloxacin, levofloxacin, clinafloxacin, nalidixic acid, enoxacin, grepafloxacin, levofloxacin, lomefloxacin norfloxacin, ofloxacin, trovafloxacin, olamufloxacin, cadrofloxacin, alatrofloxacin, gatifloxacin, rufloxacin, irloxacin, prulifloxacin, pazufloxacin, gemifloxacin, sitafloxacin, tosulfloxacin, amifloxacin, nitrosoxacin-A, DX-619, and ABT-492. Quinolone antibiotics include fluoroquinolones (e.g., having a fluorine substituent at the C-6 position), and non-fluoroquinolones. Also included within the scope of quinolone antibiotics are derivatives in which a quinolone is conjugated with, e.g., covalently bound to, another core structure. For example, U.S. Pub. No. 2004/0215017A1 discloses compounds in which an oxazolidinone, isoxazolinone, or isoxazoline is covalently bonded to a quinolone.

Included within the scope of quinolone antibiotics that can be potentiated by inactivation of the quinolone potentiator target genes or their expression products are compounds that have a core structure related to the 4-oxo-1,4-dihydroquinoline and 4-oxo-1,4 dihydronapthyridine systems, e.g., 2-pyridones, 2-naphthyridinones, and benzo[b]napthyridones. 2-pyridones are potent inhibitors of bacterial type II topoisomerases (Shen et al., *Curr. Pharm. Des.*, 3:169-176, 1997; Saiki et al., *Antimicrob. Agents Chemother.*, 43: 1574-1577, 1999). The core structures are depicted in FIG. 9 of US2009/0264342A1.

Also included within the scope of quinolone antibiotics that can be potentiated are compounds disclosed in US2009/0264342A1. These compounds have core structures related to the quinolone core structures depicted in FIG. 9 or 10 of US2009/0264342A1. Certain of these core structures are shown in FIGS. 11A and 11B of US2009/0264342A1. The invention encompasses the use of quinolone potentiating agents identified as described herein to potentiate these antibiotics.

In addition to the quinolone antibiotics, a variety of agents are known in the art that inhibit one or more bacterial type II topoisomerase inhibitors, some of which are structurally related to quinolones. Exemplary inhibitors that bind to GyrB include the coumarins, novobiocin and coumermycin A 1, cyclothialidine, cinodine, and clerocidin. Additional compounds that are reported to bind to and/or inhibit gyrase, topoisomerase IV, or both, are disclosed in U.S. Pat. Nos. 6,608,087 and 6,632,809 and in U.S. Pub. Nos. 2004/0043989A1 and 2005/0054697A1. The present invention encompasses the use of quinolone potentiating agents to potentiate any of these agents, e.g., for use in combination with any of these compounds or any compound that inhibits one or more microbial type II topoisomerases.

Aminoglycosides

Aminoglycosides are a group of antibiotics that are effective against certain types of bacteria. Examples of aminoglycosides include amikacin, gentamicin, kanamycin, neomycin, netilmicin, paromomycin, streptomycin, tobramycin, and apramycin. Those which are derived from *Streptomyces* genus are named with the suffix -mycin, while those which are derived from micromonospora are named with the suffix -micin.

Peptide Antibiotics

Over 400 natural antimicrobial peptides have been isolated and characterized. Based on chemical structure, these peptides may be classified into two main groups: linear and cyclic (Hancock et al., *Adv. Microb. Physiol.*, 1995, 37: 135-137; Kleinkauf et al., *Criti. Rev. Biotechnol.*, 198, 8: 1-32; D. Perlman et al., *Annu. Rev. Biochem.*, 1971, 40: 449-464). The mode of action for the majority of these peptides (both linear and cyclic) is believed to involve membrane disruption, leading to cell leakage (Mor, *Drug Develop. Res.*, 2000, 50: 440-447). The linear peptides, such as magainins and melitting, exist mainly as a-helical amphipathic structures (containing segregated hydrophobic and hydrophilic moieties), or as β-helices as found in gramicidin A (GA). Cyclic peptides, which mainly adopt an amphipatic β-sheet structures can be further divided into two subgroups: those containing disulfide bonds, such as tachyplesin, and those that do not, such as gramicidin S (Audreu et al., *Biopolymers*, 1998, 47: 415-433).

Peptide antibiotics also fall into two classes: non-ribosomally synthesized peptides, such as the gramicicins, polymyxins, bacitracins, glycopeptides, etc., and ribosomally synthesized (natural) peptides. The former are often drastically modified and are largely produced by bacteria, whereas the latter are produced by all species of life (including bacteria) as a major component of the natural host defense molecules of these species.

In certain embodiments, the peptide antibiotic is a lipopeptide antibiotic such as colistin, daptomycin, surfactin, friulimicin, aculeacin A, iturin A, and tsushimycin.

The RelA enzyme inhibitor and the bactericidal antibiotic act on the bacteria by different mechanisms, and a therapeutically effective amount and the duration of treatment of each could be determined by the skilled person. The molar ratio of RelA enzyme inhibitor to the bactericidal antibiotic can range from 10,000:1 to 1:10,000, or 1,000:1 to 1:1,000, or 1:1 to 1:10,000, or 10,000:1 to 1:1, or 500:1 to 1:500, or 500:1 to 1:1, or 1:1 to 1:500, or 100:1 to 1:100, or 100:1 to 1:1, or 1:1 to 1:100, or 50:1 to 1:50.

The following examples are illustrative, but not limiting, of the compositions of the present disclosure. Other suitable modifications and adaptations of the variety of conditions and parameters normally encountered in the field, and which are obvious to those skilled in the art, are within the scope of the disclosure.

RelA Enzyme Inhibitor Compounds

Lead Compound Discovery: Predicted binding scores for binding the RelA enzyme inhibitor compound to the RelA enzyme protein used the RelA enzyme protein structure from PDB file 5IQR (Structure of RelA bound to 70S ribosome) from Brown 2016. The goal is to analyze for the competitive inhibition of GTP. The higher the difference in binding energy of the RelA enzyme inhibitor compound to the RelA enzyme protein when compared to GTP to the RelA enzyme protein, the better the relative binding. The following program and computational parameters were used:

Compound Docking Information
Parent Company: Schrödinger, LLC
Docking Program: Glide Docking
PDB Structure: PDB Database 5IQR Minimized using Force Field=OPLS-2005

Compounds Minimized: Force Field=MMFF
Binding Site Grid Dimensions:
Grid Center x=297.686, y=163.654, z=226.204
Number of points (grid size) x=70, y=70, z=70
Spacing (Å)=0.375
Additional Info:
Compounds' binding energy (kcal/mol)
Binding energy Difference (kcal/mol) compound compared to GTP Using the PDB file 5IQR (Structure of RelA bound to 70S ribosome) as described above, two lead compounds were discovered. These RelA enzyme inhibitor compounds were found using a ChemBridge screening library of over 1.1 million druglike components. These compounds were purchased from Hit2Lead and utilized in the cellular assays. The compounds are outlined in Table 1.

TABLE 1

Lead compounds

| Compound Structure | IUPAC Name | Assay Name |
|---|---|---|
| 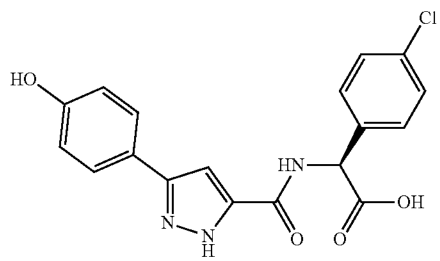 [SMILES: O=C(N[C@H](C(=O)O)c1ccc(Cl)cc1)c1cc(-c2ccc(O)cc2)n[nH]1] | (4-chlorophenyl)([(3-(4-hydroxyphenyl)-1H-pyrazol-5-yl]carbonyl)amino)acetic acid | S3-G1A |
| 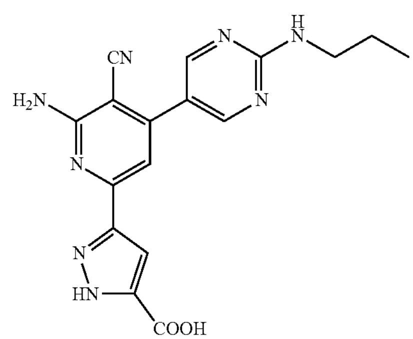 [SMILES: CCCNc1ncc(-c2cc(-c3cc(C(=O)O)[nH]n3)nc(N)c2C#N)cn1] | 3-(6-amino-5-cyano-4-[2-(propylamino)pyrimidin-5-yl]pyridin-2-yl))-1H-pyrazole-5-carboxylic acid | S3-G1B |

Modification of Lead Compounds: The two compounds of S3-G1A and S3-G1B were then modified with favorable bioisosteric replacement which increase compounds target enzyme substrate binding, human solubility, permeability, nontoxicity, and/or metabolic stability. These novel compounds are outlined in Table 2.

TABLE 2

Novel Computationally Proposed Compounds for Synthesis

| Compound Structure | IUPAC Name |
|---|---|
| 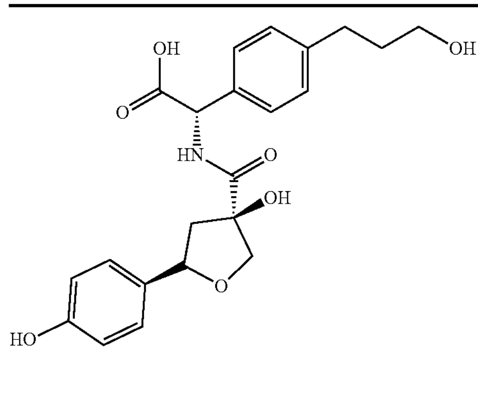 | (S)-2-((3R,5S)-3-hydroxy-5-(4-hydroxyphenyl)tetrahydrofuran-3-carboxamido)-2-(4-(3-hydroxypropyl)phenyl)acetic acid |

TABLE 2-continued

Novel Computationally Proposed Compounds for Synthesis

| Compound Structure | IUPAC Name |
|---|---|
| | (S)-2-(4-chlorophenyl)-2-(4-hydroxy-3-(4-hydroxyphenyl)-1H-pyrazole-5-carboxamido)acetic acid |
| | (S)-2-(4-chlorophenyl)-2-(4-hydroxy-3-(4-hydroxyphenyl)-1H-pyrazole-5-carboxamido)acetic acid |
| 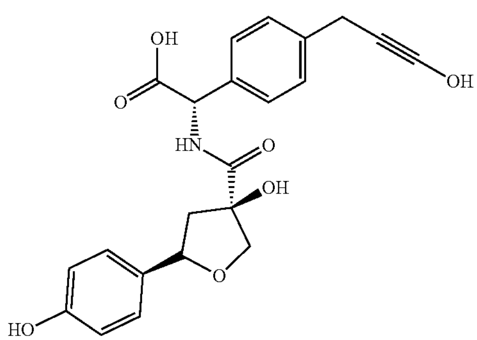 | (S)-2-((3R,5S)-3-hydroxy-5-(4-hydroxyphenyl)tetrahydrofuran-3-carboxamido)-2-(4-(3-hydroxyprop-2-yn-1-yl)phenyl)acetic acid |

Synthesis of Lead Compound S3-G1A: The synthesis of S3-G1A is shown in the Scheme 1 below. To synthesize the compound S3-G1A, first a methyl-ester protection was completed. Thionyl chloride was added to (S)-2-amino-2-(4-chlorophenyl)acetic acid in methanol. This gave the protected carboxylic acid methyl (S)-2-amino-2-(4-chlorophenyl)acetate. Then 3-(4-hydroxyphenyl)-1H-pyrazole-5-carboxylic acid was combined with HATU in dichloromethane/Hünig's base (9:1) to activate the carboxylic acid.

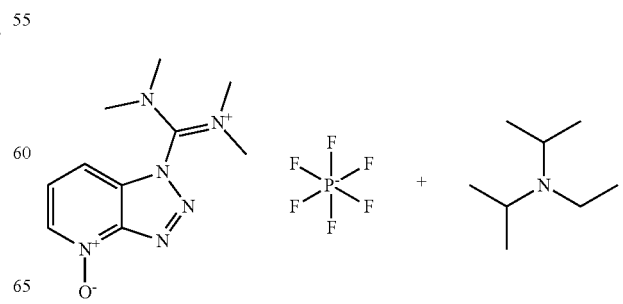

33

HATU/Hünig's Base

After 30 minutes, methyl (S)-2-amino-2-(4-chlorophenyl)acetate was added to complete the coupling. This reaction was stirred for a period of 48 hours. The afforded product, methyl (S)-2-(4-chlorophenyl)-2-(3-(4-hydroxyphenyl)-1H-pyrazole-5-carboxamido)acetate was then treated with LiOH in THF and methanol to give the final product (S)-2-(4-chlorophenyl)-2-(3-(4-hydroxyphenyl)-1H-pyrazole-5-carboxamido)acetic acid (S3-G1A) 40% yield.

34

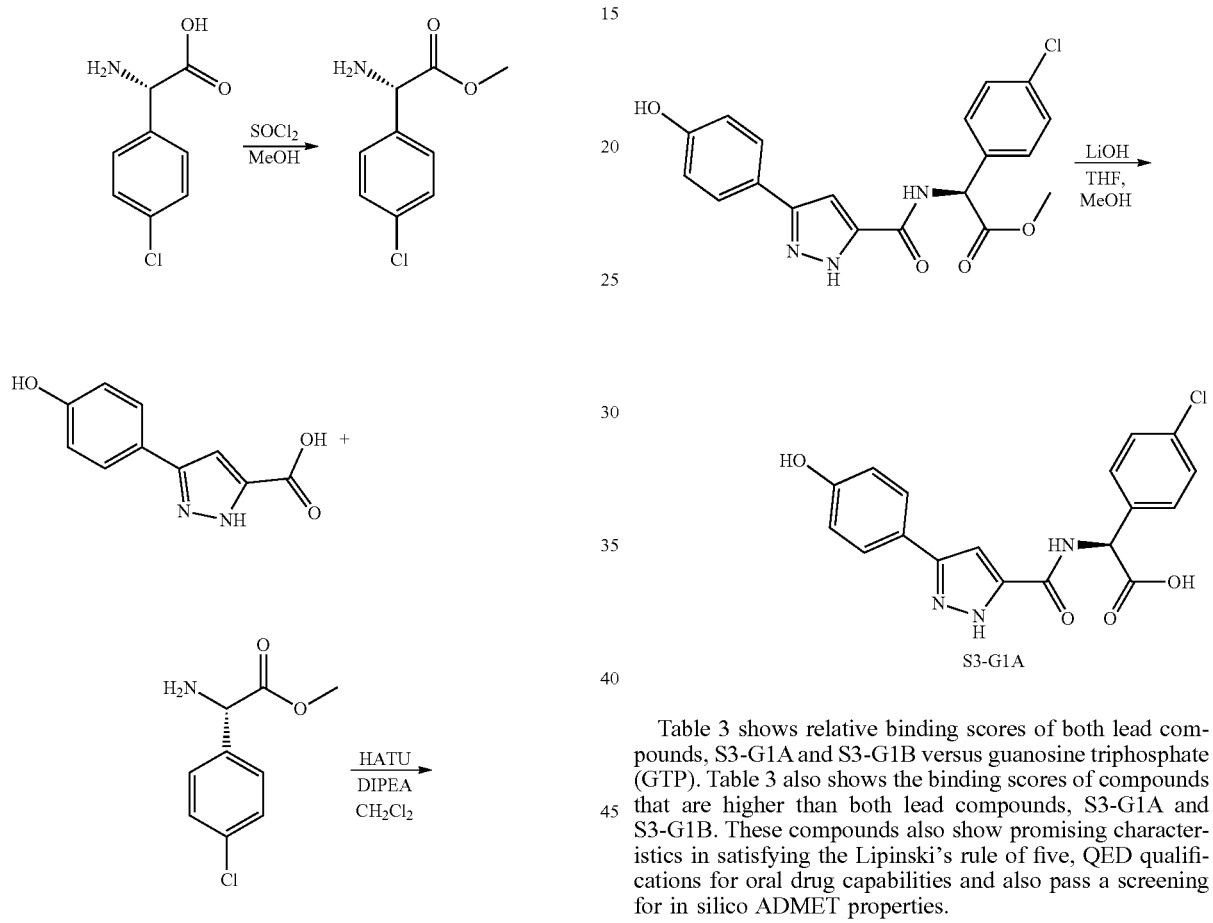

Table 3 shows relative binding scores of both lead compounds, S3-G1A and S3-G1B versus guanosine triphosphate (GTP). Table 3 also shows the binding scores of compounds that are higher than both lead compounds, S3-G1A and S3-G1B. These compounds also show promising characteristics in satisfying the Lipinski's rule of five, QED qualifications for oral drug capabilities and also pass a screening for in silico ADMET properties.

TABLE 3

| Structure | Name | Binding Energy (kcal/mol) |
|---|---|---|
| 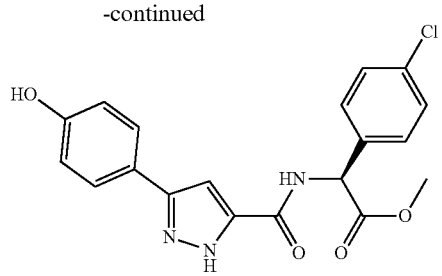 | S3-G1A (4-chlorophenyl)([(3-(4-hydroxyphenyl)-1H-pyrazol-5-yl]carbonyl)amino) acetic acid | −10.38 |

TABLE 3-continued

| Structure | Name | Binding Energy (kcal/mol) |
|---|---|---|
| 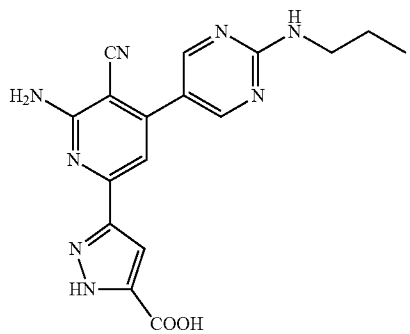 [SMILES: CCCNc1ncc(-c2cc(-c3cc(C(=O)O)[nH]n3)nc(N)c2C#N)cn1] | S3-G1B 3-(6-amino-5-cyano-4-[2-(propylamino) pyrimidin-5-yl] pyridin-2-yl))-1H-pyrazole-5-carboxylic acid | −9.64 |
| 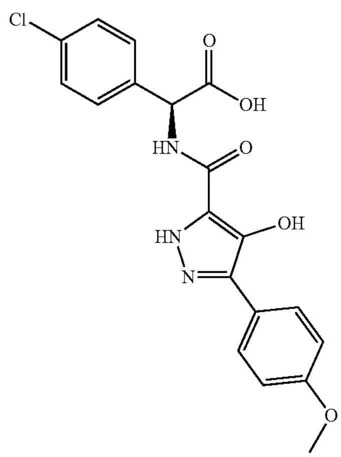 [SMILES: COc1ccc(-c2n[nH]c(C(=O)N[C@H](C(=O)O)c3ccc(Cl)cc3)c2O)cc1] | (S)-2-(4-chlorophenyl)-2-(4-hydroxy-3-(4-methoxyphenyl)-1H-pyrazole-5-carboxamido) acetic acid | −10.66 |
| 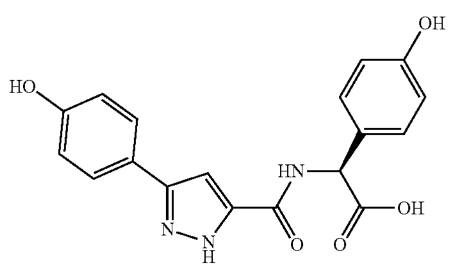 [SMILES: O=C(N[C@H](C(=O)O)c1ccc(O)cc1)c1cc(-c2ccc(O)cc2)n[nH]1] | (S)-2-(4-hydroxyphenyl)-2-(3-(4-hydroxyphenyl)-1H-pyrazole-5-carboxamido) acetic acid | −10.21 |
| 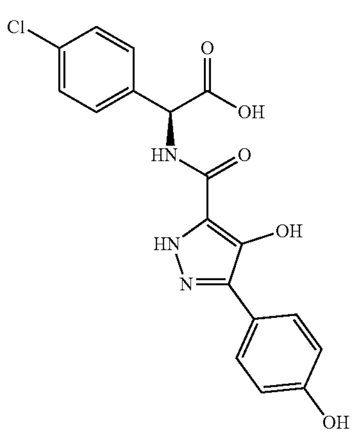 [SMILES: O=C(N[C@H](C(=O)O)c1ccc(Cl)cc1)c1[nH]nc(-c2ccc(O)cc2)c1O] | (S)-2-(4-chlorophenyl)-2-(4-hydroxy-3-(4-hydroxyphenyl)-1H-pyrazole-5-carboxamido) acetic acid | −10.65 |

TABLE 3-continued

| Structure | Name | Binding Energy (kcal/mol) |
|---|---|---|
| 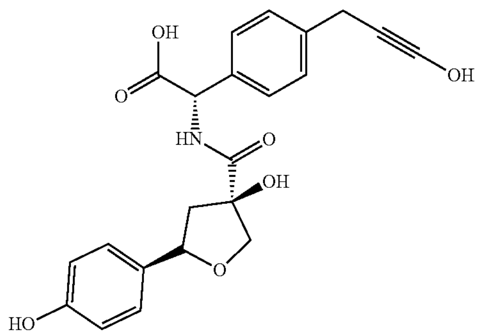 | (S)-2-((3R,5S)-3-hydroxy-5-(4-hydroxyphenyl)tetrahydrofuran-3-carboxamido)-2-(4-(3-hydroxyprop-2-yn-1-yl)phenyl)acetic acid | −13.52 |
| 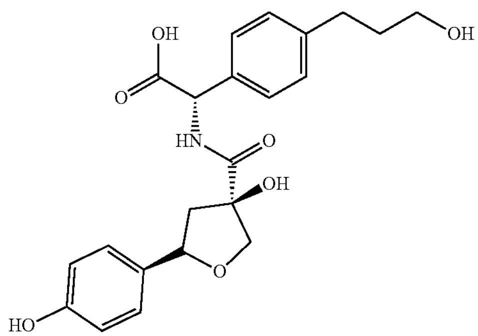 | (S)-2-((3R,5S)-3-hydroxy-5-(4-hydroxyphenyl)tetrahydrofuran-3-carboxamido)-2-(4-(3-hydroxypropyl)phenyl)acetic acid | −13.57 |
| 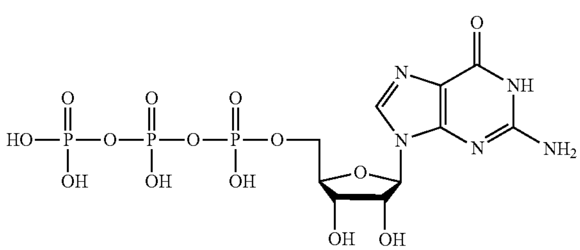 | Guanosine Triphosphate | −8.67 |

Figure 1:
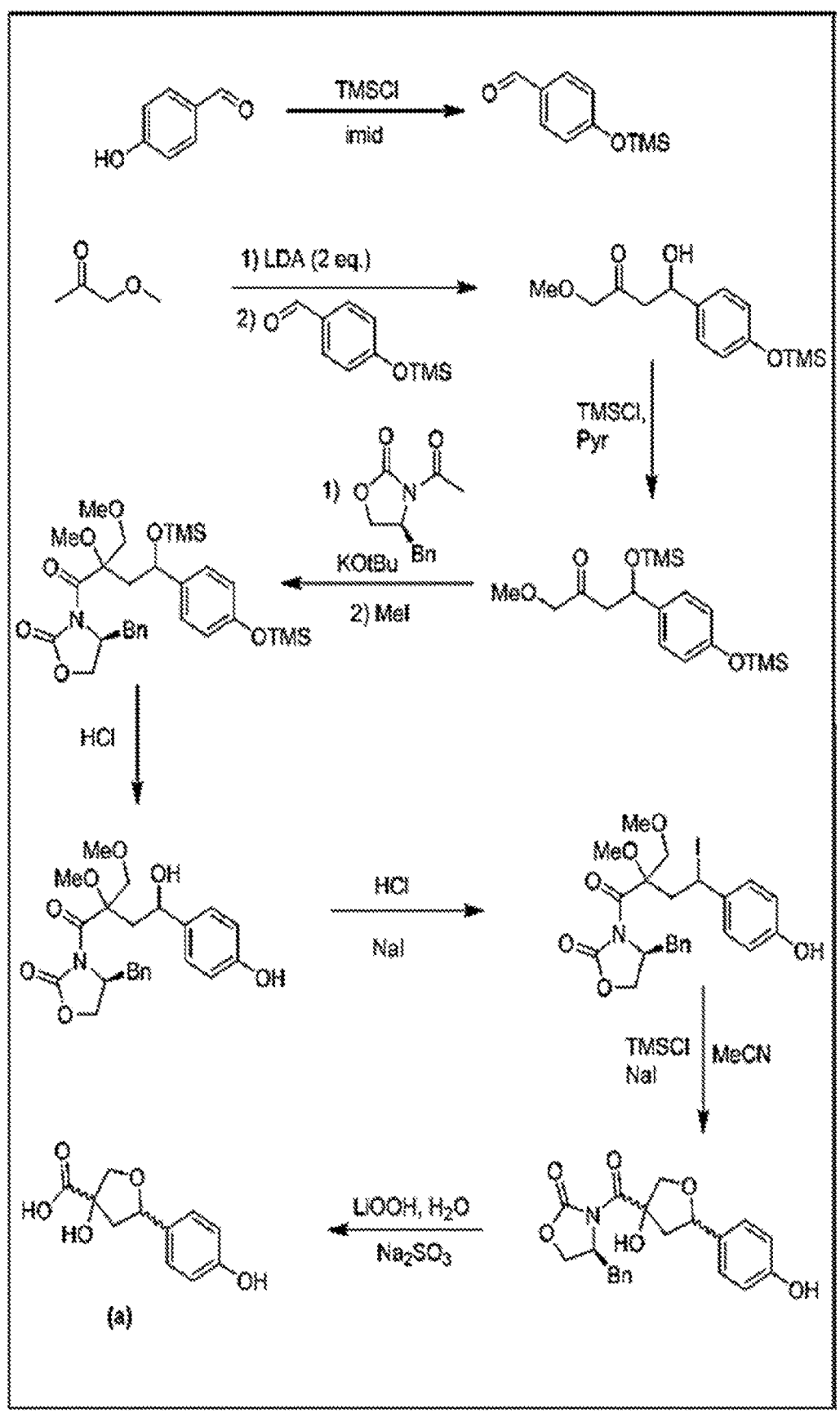
FIG. 1 is a proposed synthetic route for 2-((3R,5S)-3-hydroxy-5-(4-hydroxyphenyl)tetrahydrofuran-3-carboxamido)-2-(4-(3-hydroxypropyl)phenyl)acetic acid (c) (Ni cross coupling28).
Figure 1:
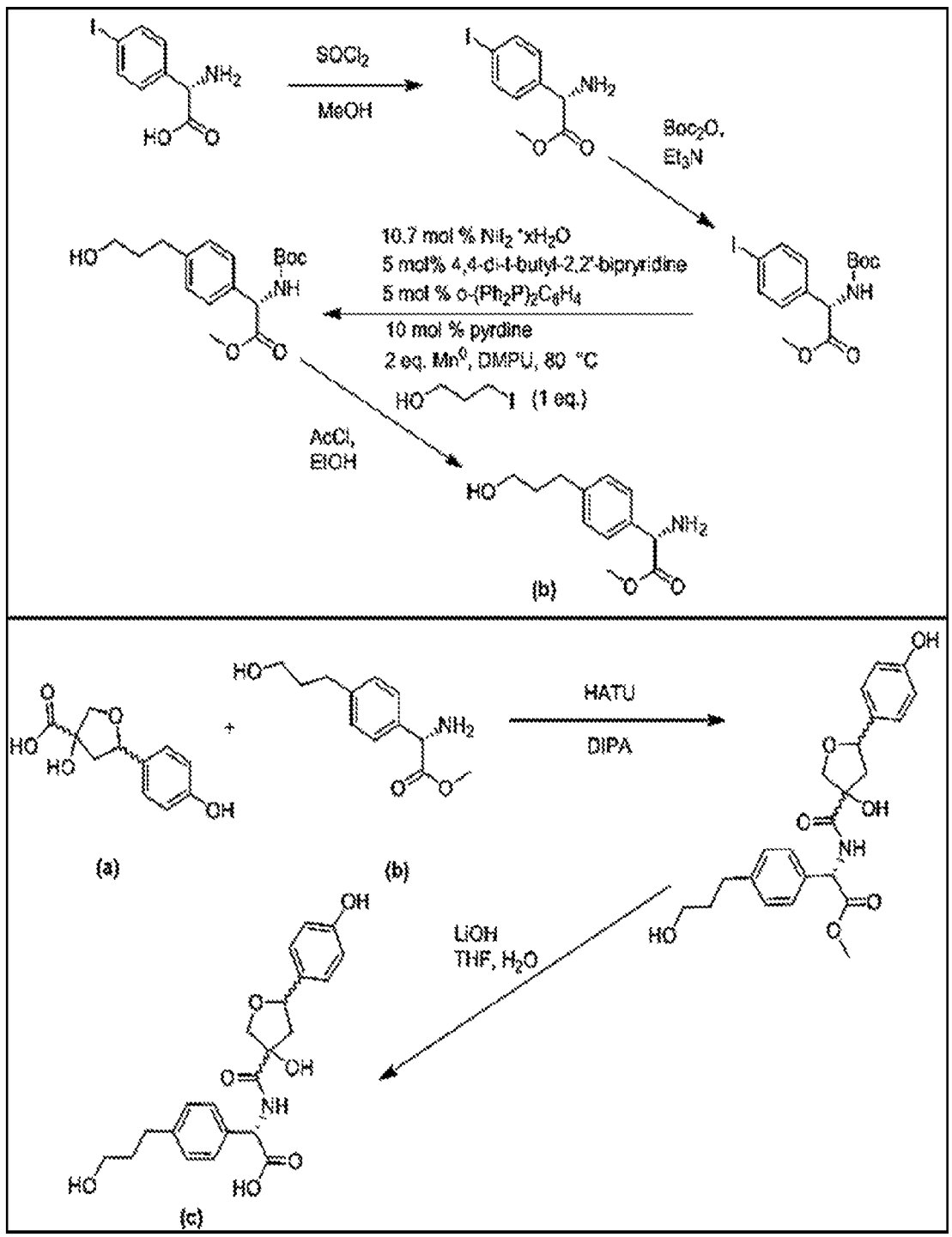

A proposed synthetic route for the production of the highest scoring compound 2-((3R,5S)-3-hydroxy-5-(4-hydroxyphenyl)tetrahydrofuran-3-carboxamido)-2-(4-(3-hydroxypropyl)phenyl)acetic acid is shown in FIG. 1. This synthesis ignores stereochemistry as a diastereomer separation may be utilized during the synthesis. However, all diastereomers were docked in silico into RelA showing binding scores above −11 kcal·mol$^{-1}$. Separation may not be necessary for compound efficacy.

Methods

The bacterial strain of *Escherichia coli* strain C was used as the model organism for initial screening. A Luria-Bertani (LB-Miller) medium was used as the full medium. Once the biofilms were grown, compounds S3-G1A and S3-G1B were tested for their ability to degrade and inhibit biofilm growth. To make sure the compounds did not directly affect the growth of the bacteria, growth curves were completed. Neither compound showed any effect on the growth of the bacteria. Compounds S3-G1A and S3-G1B also did not show any effect on the initial growth of biofilms. This is likely due to the fact that the stringent response and RelA are not active when the cells are initially grown.

Bacterial Growth—The effect of different compounds on bacterial growth was tested by adding compounds at specific concentrations to the bacterial culture (100× diluted overnight culture approx. 10$^9$ cells) in fresh LB medium. Two hundred microliters were aliquoted into a 96 well plate and placed into Biotek HT plate reader for 18 h at 37° C. Plates were shaken and the optical density (OD$_{630}$) was measured every 15 min.

Antibiotic Susceptibility Test—The antibiotic susceptibility was tested. For the liquid cultures, the minimum inhibitory concentrations (MICs) of the antimicrobial drugs were determined using 96 well plates and the broth dilution method. Suspensions were then incubated at 37° C. for 18 hours in the Biotek HT plate reader (see bacterial growth). For biofilm, the Biofilm Destruction Test discussed below was used with different antibiotic concentrations and the cell density was measured after 18 h. Bacterial concentration was calculated through optical density (OD$_{630}$), and the lowest concentration causing 80% growth inhibition relative to the growth of the control was deemed to be the MIC.

Biofilm Inhibition Test—The biofilm inhibition was analyzed. For biofilm formation on a polystyrene surface, flat-bottom 96-well microtiter plates (Corning Inc.) were used. The effect of different compounds on biofilm formation was tested by adding compounds at specific concentrations to the bacterial culture (100× diluted overnight culture approx. $10^9$ cells) in fresh LB medium. Two hundred microliters were aliquoted into 96 well plate and placed for 24 or 48 h into 37° C. incubator. Cell density was measured ($OD_{600}$) using a Multiscan Go plate reader (ThermoFisher), and 30 μL of Gram crystal violet (Remel-3 g CV, 50 mL isopropanol, 50 mL ethanol and 900 mL of purified water) was applied for staining for 1 h. Plates were washed with water and air dried, and crystal violet was solubilized with an ethanol-acetone (4:1) solution. The $OD_{570}$ was determined from this solution, and the biofilm amount was calculated as the ratio of $OD_{570}$ to $OD_{600}$.

Biofilm Destruction Test—The biofilm destruction was determined. Biofilms were grown for 24 or 48 h as described above. After that time planktonic cells were removed, and biofilms were washed twice with 250 μL of sterile phosphate buffered saline (PBS) solution. Two hundred microliters of fresh LB medium with specific concentration of the tested compounds were dispensed into wells. After 18 h incubation at 37° C., the amount of biofilm was measured by CV staining as described above.

The synergistic effect of compounds combined with antibiotics was tested. Biofilms were grown for 24, 48 or 72 h as described above. After that time planktonic cells were removed, and biofilms were washed twice with 250 μL of sterile phosphate buffered saline (PBS) solution. Two hundred microliters of fresh LB medium with specific concentration of the tested compounds and Ampicillin were dispensed into wells. After 18 h incubation at 37° C., the amount of biofilm was measured by CV staining as described above. For alamarBlue viability test, 4 μL of alamarBlue (Invitrogen) was added and plates were incubated in the Biotek HT plate reader at 37° C. for 4 h. Cell viability was measured as fluorescence at 530/590 nm (excitation/emission) versus compound concentration or initial cell density.

Results

RelA Enzyme Inhibitors Did Not Affect Bacterial Growth Rate.

Figure 2:
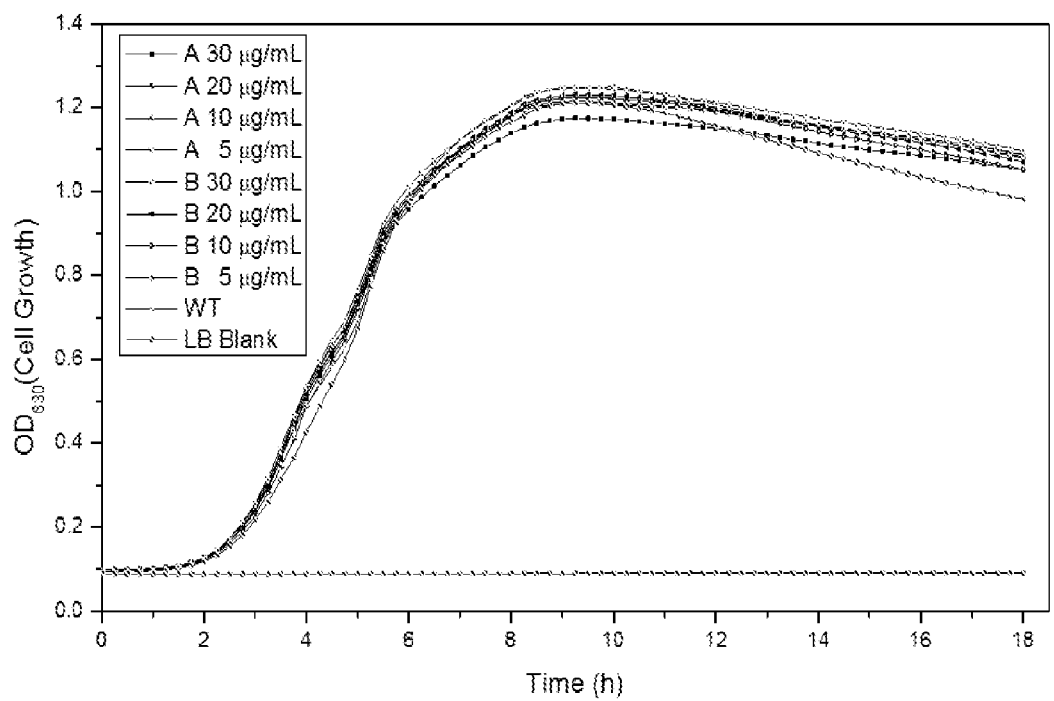
FIG. 2 shows the effect of compounds S3-G1A and S3-G1B on *E. coli* C growth.

In order to test the effect of compounds on bacterial growth, liquid culture experiments were performed. The S3-G1A compound (hereinafter "compound A") and S3-G1B compound (hereinafter "compound B") were applied to the bacterial cultures at the concentrations of 30, 20, 10 and 5 μg/mL. The differences in bacterial growth curves in liquid cultures fortified with the test compounds were measured. The growth curves are shown in FIG. 2.

The results showed that the growth of *E. coli* C was not inhibited by any of the compounds at the tested concentrations.

Effect of Antibiotic Concentration on Planktonic Cells and Biofilm.

The *Escherichia coli* strain C is sensitive to all types of antibiotics. To test the MIC of ampicillin, a standard growth curve experiment was run with different concentrations of antibiotics. The results showed the change in growth curves with the increased drug concentration (FIG. 3). Although ampicillin is a bactericidal antibiotic, at low concentrations it showed more of a bacteriostatic effect with a prolonged lag phase. FIG. 3 shows the effect of different ampicillin concentrations on planktonic growth of *E. coli* C. Inoculum at 1000× dilution of overnight culture.

As cells in the biofilm tend to be more resistant to antibiotics, similar ampicillin concentration was tested to check the effect of 18 h antibiotic treatment on 2-day biofilm growth. The results showed that at low concentrations (10-30 μg/ml) cell density is similar to the untreated control (FIG. 4). At 40 μg/mL, a decrease in cell growth was observed of 15%. Starting from 50 μg/mL the cell density was reduced from 53% to 5% (at 90 μg/mL) of the untreated control.

Small Molecules Do Not Affect Biofilm Formation

In order to check the effect of small molecules on biofilm formation, a biofilm inhibition experiment was designed. Compounds A and B were tested at concentration 20 μg/mL. The Innate defense regulator peptide-1018 (IDR-1018) (10 μg/mL) and serine hydroxamate (1 μg/mL) were also included.

Figure 5A:
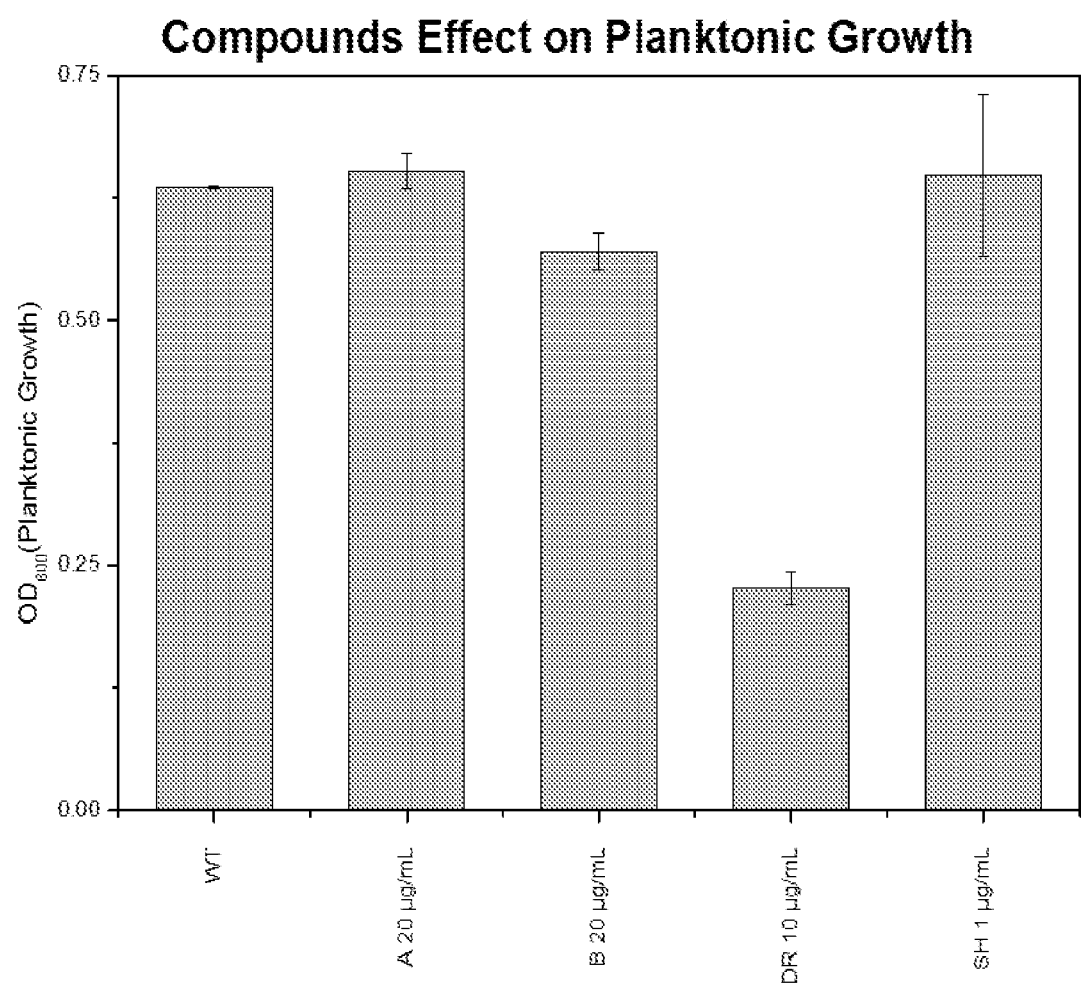
Figure 5B:
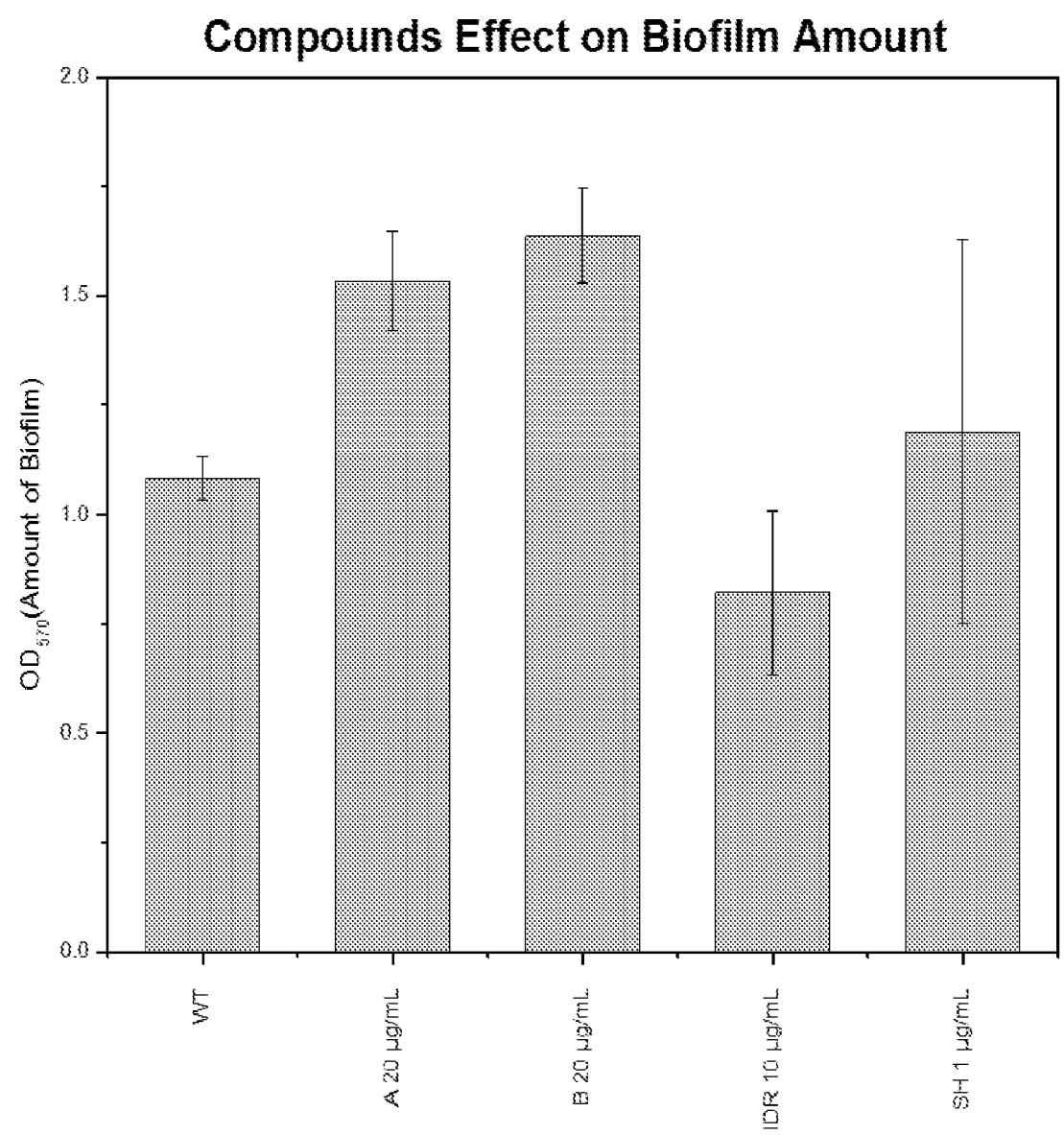

Both compounds A and B had no effect on the growth rate (FIG. 2), and therefore, it was expected that also in this experiment, the planktonic cell density would not be affected (FIG. 5A). Only a slight increase in biofilm formation was observed for compounds A and B (FIG. 5B) as measured with crystal violet. The darker the wells (crystal violet stained biofilm) the higher the concentration of biofilm that have formed. As IDR-1018 had been previously described to have a strong effect on both planktonic and biofilm cells, it was used as the control. IDR-1018 is a non-druggable antibiofilm peptide. IDR-1018 is a known biofilm disruptor that directly acts and degrades (p)ppGpp in cells (de la Fuente-Núñez et al. *PLOS Pathogens* 2014, 10 (5), e1004152). At 10 μg/mL of IDR-1018, both planktonic growth and biofilm were lower than the untreated control by 63% and 45%, respectively (FIGS. 5A and 5B). Serine hydroxamate, which is a stringent response inducer, did not show any effect in the 24 h experiment.

Small Molecules Do Not Affect Biofilm Persistence.

The effect of small molecules on biofilm persistence was tested. Two days biofilms were treated with compounds A and B as well as IDR-1018 and serine hydroxamate. Results showed that both compounds had no significant effect on biofilm survival (FIG. 6). IDR-1018 showed a smaller effect on biofilm destruction than on biofilm inhibition.

Antibiotic Stress Prevents Biofilm Destruction and Increases Biofilm Persistence As described above, antibiotics affect bacterial cell survival in biofilms. Thus, the effect of antibiotic on biofilm persistence was tested. Ampicillin was applied on 2 days old biofilm and the amount of biofilm was analyzed after 18 h. Bacterial cell densities were measured and showed the same trend as above with lower cell density at higher ampicillin concentration (FIG. 4). Biofilm analysis of the same samples showed an increase in biofilm persistence (FIG. 7) from 1.7 (Amp 10) to 5.9-fold (for Amp 70).

Synergy Between Small Molecules and Antibiotics to Destruct Biofilm.

The results confirm that the RelA enzyme inhibitor compounds of the present invention have the ability to decompose *E. Coli* biofilms in combination with antibiotics. FIG. 8 highlights some of the data collected. When the compounds are used in conjunction with ampicillin they have the effect of decreasing the biofilm concentration significantly compared to that of the biofilms treated with just antibiotics. As a positive control in these experiments IDR-1018 was utilized. IDR-1018 is a non-druggable antibiofilm peptide. IDR 1018 is a known biofilm disruptor that directly acts and degrades (p)ppGpp in cells (de la Fuente-Núñez 2014). The results show compounds S3-G1A and S3-G1B outperform IDR-1018.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

All documents mentioned herein are hereby incorporated by reference in their entirety or alternatively to provide the disclosure for which they were specifically relied upon. The applicant(s) do not intend to dedicate any disclosed embodiments to the public, and to the extent any disclosed modifications or alterations may not literally fall within the scope of the claims, they are considered to be part hereof under the doctrine of equivalents.

We claim:
1. A pharmaceutical composition comprising a RelA enzyme inhibitor and a bactericidal antibiotic, wherein said RelA enzyme inhibitor binds to RelA enzyme and the RelA inhibitor is a compound selected from compounds of the Formulae I and II:

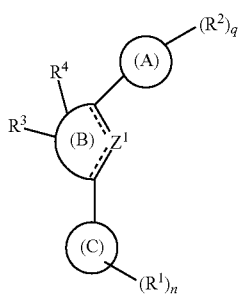

Formula I

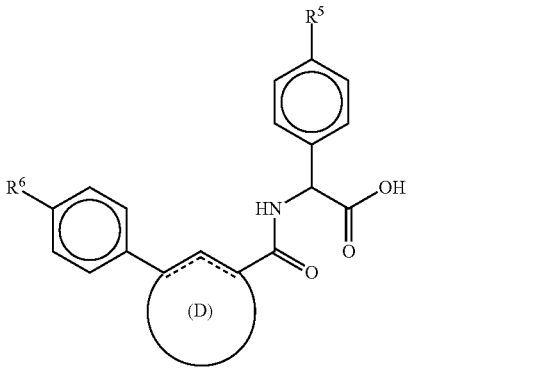

Formula II in Formula I, Ring (A) and Ring (C) are each bonded to carbon atoms of Ring (B) meta to one another;
n is 1 or 2,
q is 1 or 2,
$R^1$ and $R^2$ are each individually selected from the group consisting of hydrogen, carboxylic acid, carboxylic $C_{1-6}$ alkyl ester, hydroxyl, amino, $C_{1-6}$ alkyl amino, and amino $C_{1-6}$ alkyl;
Ring (A) is a 6 membered ring selected from the group consisting of pyridine, pyrimidine, pyridazine, pyran, oxazine, thiazine, and piperazine;
Ring (B) is a 6 membered pyridine ring, $Z^1$ is a ring member of Ring (B) and $Z^1$ is nitrogen or a carbon substituted with hydrogen, amino or $C_{1-3}$ alkyl, ⸺ is a single bond, double bond or a bond in the aromatic ring, $R^3$ and $R^4$ are substituents on ring carbon atoms and are each individually selected from the group consisting of hydrogen, cyano, amino and $C_{1-3}$ alkyl; and
Ring (C) is a 5 membered ring selected from the group consisting of pyrazole, pyrole, furan, tetrahydrofuran, and tetrahydrothiophene;

in Formula II, Ring (D) is substituted at a first ring carbon with phenyl-$R^6$ and Ring (D) is substituted at a second ring carbon with the carbonyl of the amide group, and wherein the first ring carbon and the second ring carbon are each bonded to the same third ring carbon of Ring (D),
$R^5$ is selected from the group consisting of hydrogen, halogen, hydroxyl, optionally substituted $C_{1-6}$ alkyl, optionally substituted $C_{3-6}$ alkyne, wherein the optional substituent(s) are each individually selected from the group consisting of carboxylic acid, carboxylic $C_{1-3}$ ester, $C_{1-6}$ alkyl, halogen, $C_{1-6}$ alkoxy, hydroxyl, amino, $C_{1-6}$ alkyl amino, and amino $C_{1-6}$ alkyl;
$R^6$ is selected from the group consisting of hydrogen, hydroxyl, and optionally substituted $C_{1-6}$ alkoxy, wherein the optional substituent(s) are each individually selected from the group consisting of carboxylic acid, carboxylic $C_{1-3}$ ester, $C_{1-6}$ alkyl, halogen, $C_{1-6}$ alkoxy, hydroxyl, amino, $C_{1-6}$ alkyl amino, and amino $C_{1-6}$ alkyl; and
Ring (D) is an optionally substituted 5-membered heterocycle selected from the group consisting of pyrazole, tetrahydrofuran, and tetrahydrothiophene, wherein the optional substituent(s) are each individually selected from the group consisting of hydrogen, carboxylic acid, carboxylic $C_{1-3}$ ester, $C_{1-6}$ alkyl, halogen, $C_{1-6}$ alkoxy, hydroxyl, amino, $C_{1-6}$ alkyl amino, and amino $C_{1-6}$ alkyl; ⸺ is a single bond, double bond or a bond in the aromatic ring;
and pharmaceutically acceptable salts of any of the foregoing compounds.

2. The pharmaceutical composition of claim 1, wherein the RelA enzyme inhibitor binds to the RelA enzyme with a predicted binding score which is less than or equal to −9 kcal/mole.

3. The pharmaceutical composition of claim 1, wherein the RelA enzyme inhibitor is selected from the group consisting of S3-G1A and S3-G1B:

| Compound Structure | IUPAC Name | Assay Name |
|---|---|---|
| ![S3-G1A structure] | (4-chlorophenyl)([[3-(4-hydroxyphenyl)-1H-pyrazol-5-yl]carbonyl)amino)acetic acid | S3-G1A |

| Compound Structure | IUPAC Name | Assay Name |
|---|---|---|
| 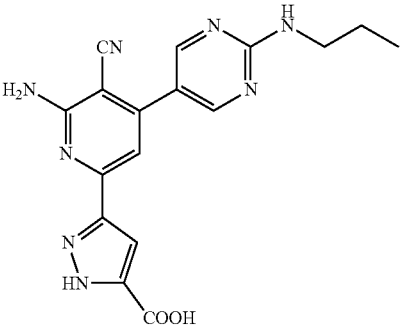 | 3-(6-amino-5-cyano-4-[2-(propylamino)pyrimidin-5-yl]pyridin-2-yl))-1H-pyrazole-5-carboxylic acid | S3-G1B. | and a pharmaceutically acceptable salt of S3-G1A and S3-G1B.

4. The pharmaceutical composition of claim 1, wherein the RelA enzyme inhibitor is selected from the group consisting of one of the following compounds or a pharmaceutically acceptable salt thereof:

| Compound Structure | IUPAC Name |
|---|---|
| 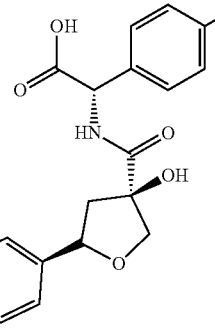 | (S)-2-((3R,5S)-3-hydroxy-5-(4-hydroxyphenyl)tetrahydrofuran-3-carboxamido)-2-(4-(3-hydroxypropyl)phenyl)acetic acid |
| 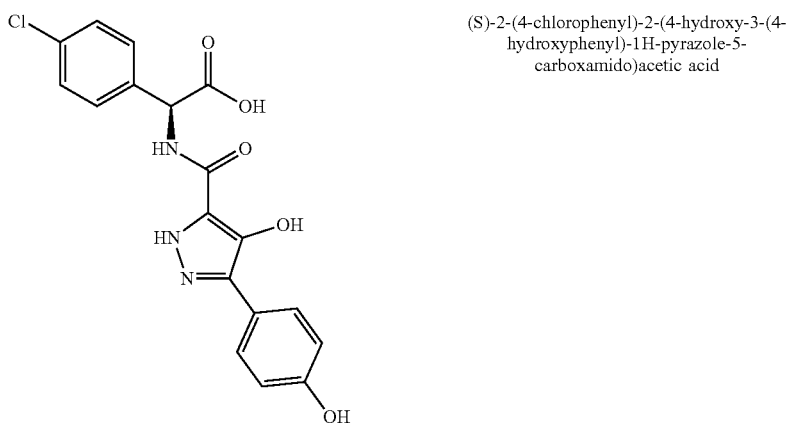 | (S)-2-(4-chlorophenyl)-2-(4-hydroxy-3-(4-hydroxyphenyl)-1H-pyrazole-5-carboxamido)acetic acid |

| Compound Structure | IUPAC Name |
| --- | --- |
| (structure) | (S)-2-(4-chlorophenyl)-2-(4-hydroxy-3-(4-methoxyphenyl)-1H-pyrazole-5-carboxamido)acetic acid |
| (structure) | (S)-2-((3R,5S)-3-hydroxy-5-(4-hydroxyphenyl)tetrahydrofuran-3-carboxamido)-2-(4-(3-hydroxyprop-2-yn-1-yl)phenyl)acetic acid. |
| (structure) | (S)-2-(4-hydroxyphenyl)-2-(3-(4-hydroxyphenyl)-1H-pyrazole-5-carboxamido)acetic acid |

5. The pharmaceutical composition of claim 1, wherein the bactericidal antibiotic is selected from the group consisting of an aminoglycoside, an aminomethylcycline, an aminophenicol, an ansamycin, a β-lactam, a carbapenem, a dapsone, a 2,4-diaminopyrimidine, a glycopeptide, a glycycycline, a ketolid, a lincomycin, a lincosamide, a macrolide, a nitrofuran, an oxazolidinone, a peptide, a polymyxin, a quinolone, a rifabutin, a streptogramin, a sulfonamide, a sulfone, a tetracycline, and combinations thereof.

6. The pharmaceutical composition of claim 5, wherein the bactericidal antibiotic is kanamycin, norfloxacin, or ampicillin.

* * * * *